(12) United States Patent
Khurana Hershey et al.

(10) Patent No.: US 7,919,240 B2
(45) Date of Patent: Apr. 5, 2011

(54) ALTERED GENE EXPRESSION PROFILES IN STABLE VERSUS ACUTE CHILDHOOD ASTHMA

(75) Inventors: Gurjit K. Khurana Hershey, Cincinnati, OH (US); Bruce Aronow, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 1291 days.

(21) Appl. No.: 11/314,565

(22) Filed: Dec. 21, 2005

(65) Prior Publication Data

US 2007/0141585 A1 Jun. 21, 2007

(51) Int. Cl.
*C12Q 1/68* (2006.01)
*C12P 19/34* (2006.01)
(52) U.S. Cl. ............................ 435/6; 435/91.1; 435/91.2
(58) Field of Classification Search .................. None
See application file for complete search history.

(56) References Cited

U.S. PATENT DOCUMENTS

2003/0166562 A1* 9/2003 Rothenberg et al. ............ 514/12

OTHER PUBLICATIONS

Golub et al., "Molecular Classification of Cancer: Class Discovery and Class Prediction by Gene Expression Monitoring" Science, 1999, vol. 286, pp. 531-537.*
Bertorelli et al., "Heat shock protein 70 upregulation is related to HLA-DR expression in bronchial asthma. Effects of inhaled glucocorticoids," Clinical and Experimental Allergy, 1998, vol. 28, pp. 551-560.*
Karp CL, et al., Identification of complement factor 5 as a susceptibility locus for experimental allergic asthma, Nat'l Immunol (2000); 1: pp. 221-226.
Zimmerman, et al. "Dissection of experimental asthma with DNA microarray analysis identifies arginase in asthma pathogenesis", J Clin Invest, (2003); 111: pp. 1863-1874.
Zou, J. et al., "Microarray profile of differentially expressed genes in a monkey model of allergic asthma" Genome Bio (2002) 3: pp. 1-13.
Brutsche MH, et al. "Array-based diagnostic gene-expression score for atopy and asthma" J Allergy Clin Immunol (2002) 109: pp. 271-273.
Yuyama, N, et al. "Analysis of novel disease-related genes in bronchial asthma" Cytokine (2002), 19: pp. 287-296.
Lee, JH, et al. "Interleukin-13 induces dramatically different transcriptional programs in three human airway cell types" Am J Respir Cell Mol Biol (2001), 25: pp. 474-485.
American Thoracic Society Lung function testing: Selection of reference values and interpretive strategies. Am Rev Respir Dis (1991) 144: pp. 1202-1218.
American Thoracic Society "Standardization of spirometry: 1994 update" Am J Respir Crit Care Med (1994) 152: pp. 1107-1136.
National Cancer Institute. Microarray tracking system NCI Affymetrix GeneChip access program. Gene Table for the HU133A chip. Bethesda (MD) (2002) Excel Spreadsheet, pp. 1-892.

Eisen, MB, et al. "Cluster analysis and display of genome-wide expression patterns" Proc Nat'l Acad Sci U S A (1998) 95: pp. 14863-14868.
Gordon,A, "Monographs on statistics and applied probability" (2nd edit p. 41-48) Boca Raton (FL): Chapman & Hall/CRC Press; 1999.
Bates, MD, et al., "Novel genes and functional relationships in the adult mouse gastrointestinal tract identified by microarray analysis" Gastroenterology (2002), 122: pp. 1467-1482.
Muller, PY, et al., "Process of gene expression data generated by quantitative RT-PCR" Biotechniques (2002) 32: pp. 1372-1374 6,8-9.
Vandesompele J, et al. "Accurate normalization of real-time quantitative RT-PCR data by geometric averaging of multiple internal control genes" Genome Biol (2002) 3: RESEARCH0034.
Joseph, CL, et al. "Racial differences in emergency department use persist despite allergist visits and prescriptions filled for antiinflammatory medications". J Allergy Clin Immunol (1998) 101: pp. 484-490.
Lester, LA, et al., "Ethnic differences in asthma and associated phenotypes: collaborative study on the genetics of asthma" J Allergy Clin Immunol (2001) 108: pp. 357-362.
McGill, KA, et al. "Asthma in non-inner city Head Start children" Pediatrics (1998) 102: pp. 77-83.
Kay, AB, "Allergy and allergic diseases: first of two parts" N Engl J. Med (2001) 334: pp. 30-37.
Kay, AB, "Allergy and allergic diseases: second of two parts" N Engl J. Med (2001) 344: pp. 103-113.
Gaga, M, et al. "Eosinophils are a feature of upper and lower airway patholgy in non-atopic asthma, irrespective of the presence of rhinitis" Clin Exp Allergy (2000) 30: pp. 663-669.
Naclerio, RM, "Allergic rhinitis" New England J. Med. (1991) 325: pp. 860-869.
Seki, Y. et al. "SOCS-3 regulates onset and maintenance of T(H)2-mediated allergic responses". Nat Med (2003) 9: pp. 1047-1054.
Humbles, AA, et al. "A role for the C3a anaphylatoxin receptor in the effector phase of asthma" Nature (2000) 406: pp. 998-1001.
Drouin SM, et al. "Expression of the complement anaphylatoxin C3a and C5a receptors on bronchial epithelial and smooth muscle cells in models of sepsis and asthma" J Immunol (2001) 166: pp. 2025-2032.
Drouin SM, "Cutting edge: the absence of C3 demonstrates a role for complement in Th2 effector functions in a murine model of pulmonary allergy" J Immunol (2001) 167: pp. 4141-4145.
Kunkel SL, et al. "The role of chemokines in the immunopathology of pulmonary disease" Forum (Genova) (1999) 9: pp. 339-355.
Matheson, JM, et al. "Importance of inflammatory and immune components in a mouse model of airway reactivity to toluene diisocyanate (TDI)." Clin Exp Allergy (2001) 31: pp. 1067-1076.
Schneider E, et al. "Trends in histamine research: new functions during immune responses and hematopoiesis". Trends Immunol (2002) 23: pp. 255-263.

(Continued)

*Primary Examiner* — Young J Kim
(74) *Attorney, Agent, or Firm* — Thompson Hine LLP

(57) ABSTRACT

Differences in gene expression in control and asthma patients to profile, differentiate, evaluate, etc. patients with exacerbated asthma and stable asthma.

12 Claims, 5 Drawing Sheets

(4 of 5 Drawing Sheet(s) Filed in Color)

OTHER PUBLICATIONS

Oda T, et al. "Molecular cloning and characterization of a novel type of histamine receptor preferentially expressed in leukocytes". J Biol Chem (2000) 275: pp. 36781-36786.

Henderson WR, et al. "Blockade of CD49d (alpha4 integrin) on intrapulmonary but not circulating leukocytes inhibits airway inflammation and hyperresponsiveness in a mouse model of asthma" J Clin Invest (1997) 100: pp. 3083-3092.

Meerschaert J, et al. "Engagement of alpha4beta7 integrins by monoclonal antibodies or ligands enhances survival of human eosinophils in vitro" J Immunol (1999) 163: pp. 6217-6227.

Guajardo, J., et al. "Altered gene expression profiles in nasal respiratory epithelium reflect stable versus acute childhood asthma", JAllergy Clin Immunol, Feb. 2005, pp. 243-251.

* cited by examiner

Figure 1
A
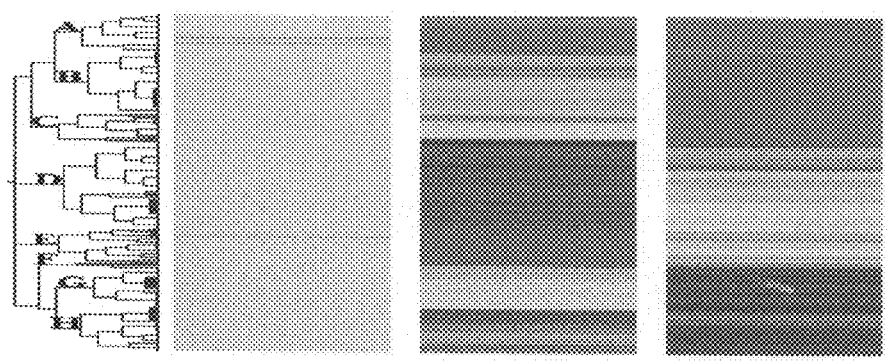
B
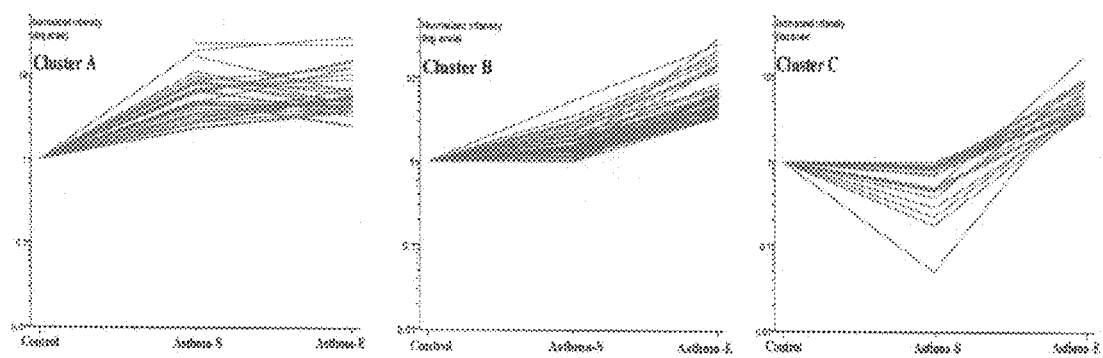
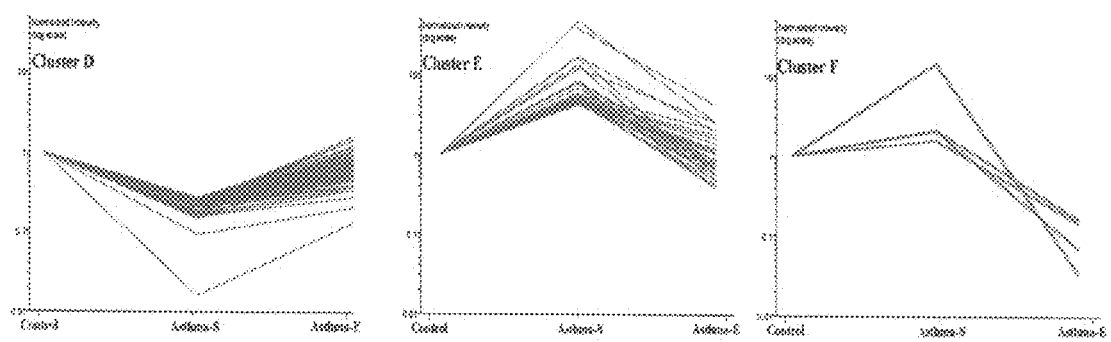
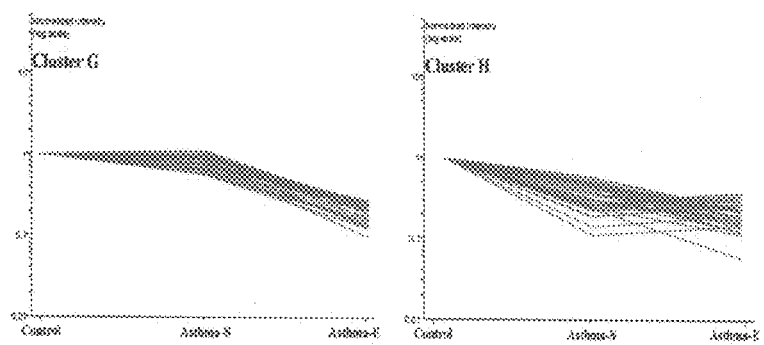

Figure 2
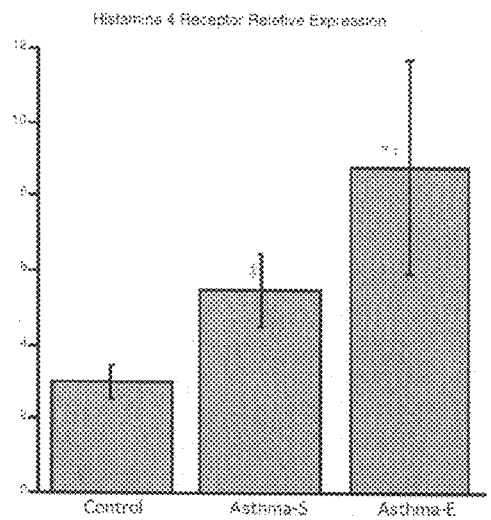
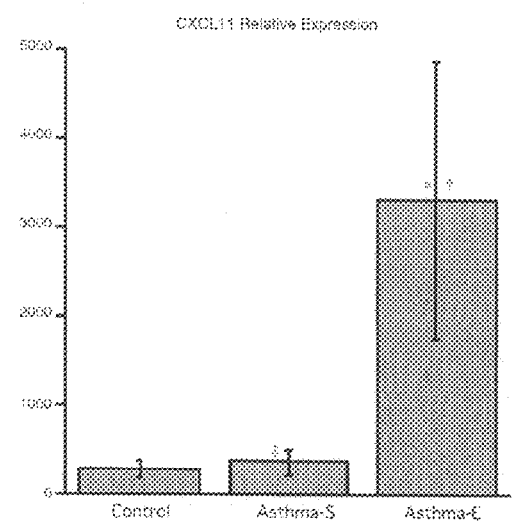
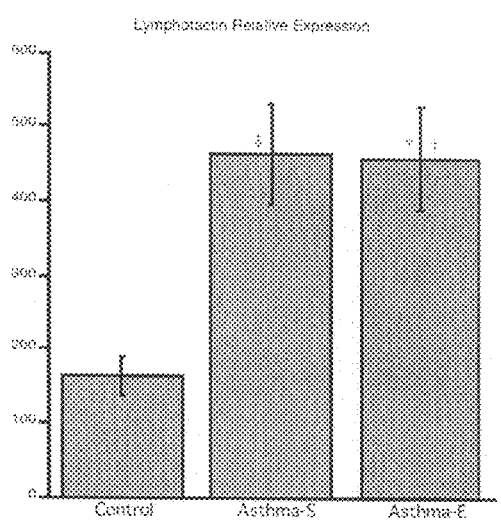
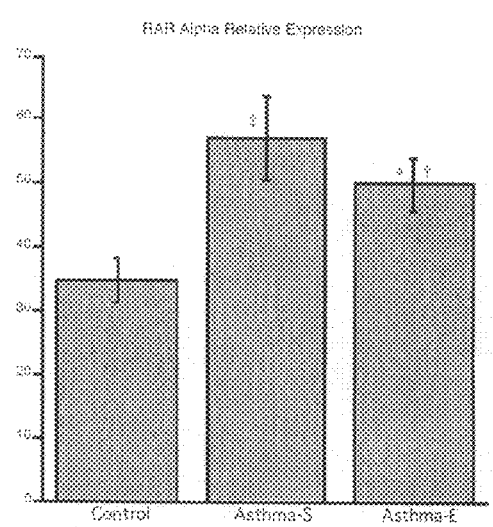

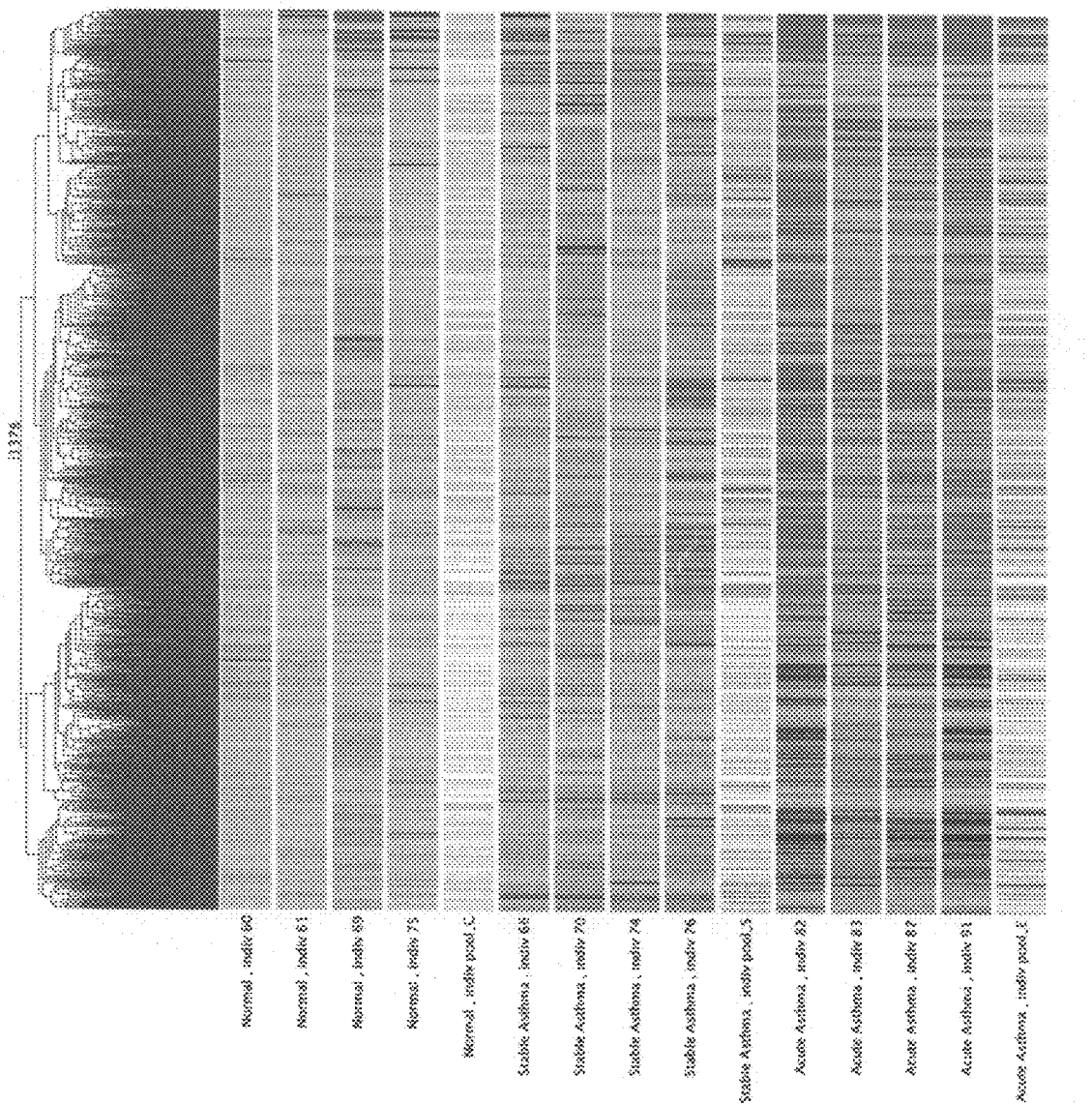

ALTERED GENE EXPRESSION PROFILES IN STABLE VERSUS ACUTE CHILDHOOD ASTHMA

This invention was made with government support under Grant Nos. R01AI46652-01A1 and R01HL72987 awarded by the National Institutes of Health. The government has certain rights in the invention.

In accordance with 37 CFR §§1.77, 1.821-1.824, and 1.52 (e), applicants state that the Sequence Listing for this application is submitted only in electronic form on a CD-ROM and herein incorporate by reference the entire Sequence Listing contained on the CD-ROM. The only material on the CD-ROM is the Sequence Listing for the instant patent application, which was created on Dec. 20, 2005 and has 616 KB. Applicants further state that the Sequence Listing information recorded and submitted herein in computer readable form is identical to the written (CD-ROM) sequence listing.

FIELD OF THE INVENTION

The invention is directed to asthma gene expression profiles.

BACKGROUND

Asthma is the most common chronic disease of childhood and has a strong genetic component. Microarray technology has been used previously to identify gene profiles associated with asthma but were limited to adult patients and to RNA derived from peripheral blood mononuclear cells. Because asthma most often begins in childhood, genes identified in adults may not represent genes important for asthma development.

SUMMARY OF THE INVENTION

Microarray technology was applied to childhood asthma. Gene profiles, also referred to herein as signatures, associated with childhood stable and exacerbated asthma, also referred to herein as acute asthma, were determined. It was also determined whether the same genes induced during stable asthma were expressed during asthma exacerbations, or whether a distinct set of genes were activated during an asthma exacerbation. Microarray technology in a group-averaged approach, and confirmatory reverse transcription polymerase chain reaction (RT-PCR) at an individual patient level, provided global gene expression profiles in respiratory epithelial cells derived from nasal respiratory epithelial cells in normal and asthmatic children.

Children with stable asthma (asthma-S), children experiencing an asthma exacerbation (asthma-E), and non-asthmatic children were evaluated. RNA was prepared from nasal respiratory epithelial cells isolated from each child, initially analyzed as pooled samples from the three groups. Further validation was performed on individual patient samples using microarrays and RT-PCR.

Distinct gene clusters were identifiable in individual and pooled asthma-S and asthma-E samples. Asthma-E samples demonstrated the strongest and most reproducible signatures, with 314 genes of 34,886 measured as Present on the chip, demonstrating induction or repression of greater than two-fold with p<0.05 in each of four individual samples. Asthma-S-regulated genes encompassed genes that overlapped with those of Asthma-E, but were fewer (166) and less consistent with respect to their behavior across the Asthma-E patient samples. Independent gene expression signatures were reflective of cells and genes poised or committed to activation by an asthma attack.

The information is useful for asthma diagnosis, evaluation of status and treatment response, and design of prophylaxis and therapy. These and other advantages will be apparent in light of the following figures, tables, and detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows hierarchical clustering and relative expression of genes highly expressed in childhood asthma.

FIG. 2 shows quantitative reverse transcription polymerase chain reaction analysis of selected genes.

FIG. 3 shows hierarchical clustering of genes highly expressed in individual children with stable and acute asthma compared with controls.

DETAILED DESCRIPTION

Figure 4A:
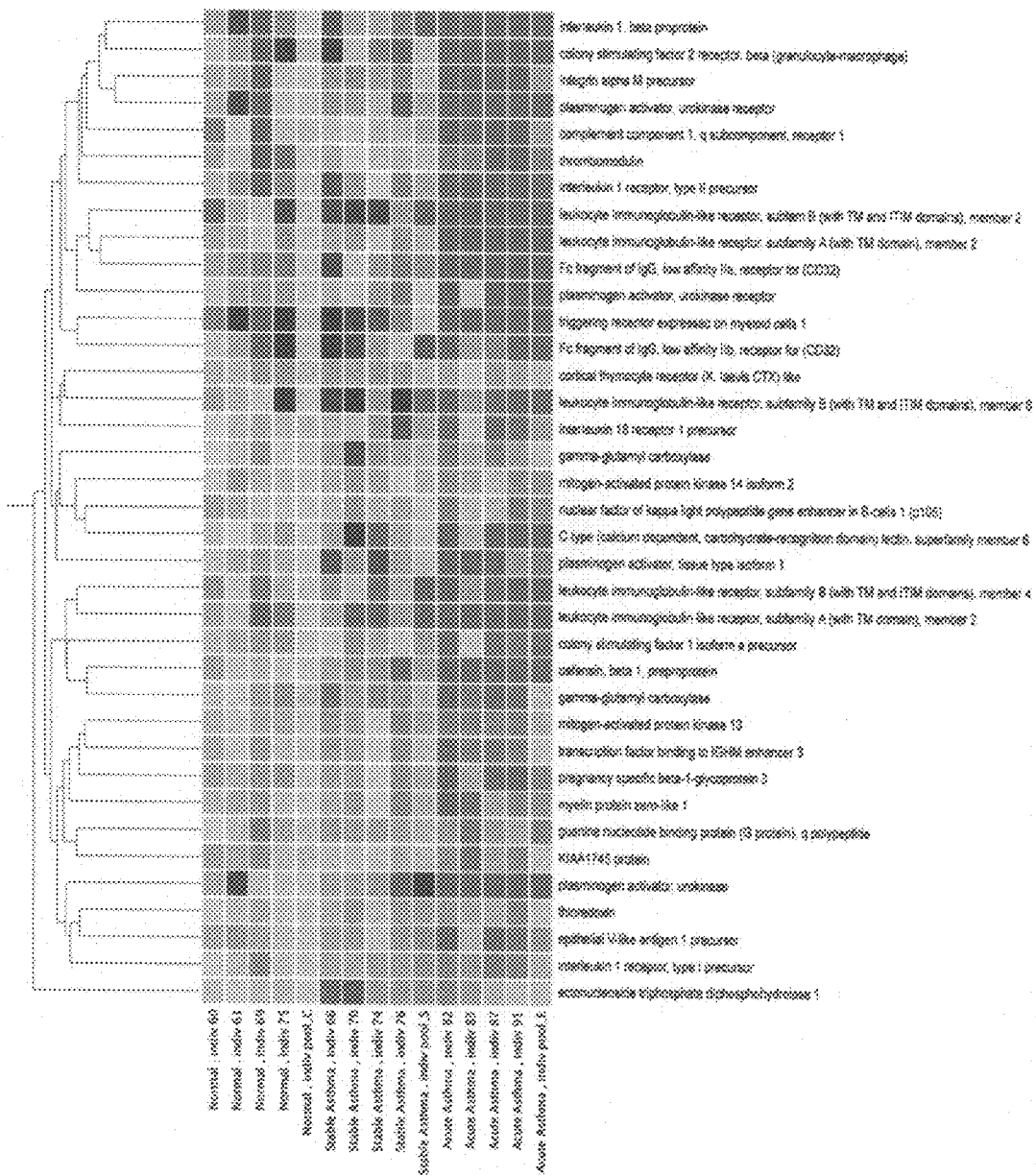
FIG. 4 shows selected upregulated and downregulated genes compared with normal controls.

Applicants incorporate by reference in its entirety Guajardo et al., Altered gene expression profiles in nasal respiratory epithelium reflect stable versus acute childhood asthma, J. Allergy Clin Immunol 2005; 115:243-53.

Healthy and asthmatic children attending the clinics and emergency department of Cincinnati Children's Hospital Medical Center (CCHMC) were evaluated. Asthmatic children were either stable, indicated by the substantial absence of wheezing, or exacerbated, indicated by wheezing. Asthma was diagnosed according to American Thoracic Society criteria. Participants were included in one of three groups: 1. Stable allergic asthma (asthma-S group, N=10) inclusion criteria: a. younger than 18 years of age, b. physician-diagnosed asthma currently stable (not wheezing), and c. positive skin prick testing to any of the allergens from an environmental panel that included dust mite, molds, cat, dog, feathers, weeds and ragweed, tree pollens and grass allergen extracts (Hollister-Stier Laboratories, Spokane Wash.); 2. Exacerbation of asthma (asthma-E group, N=10) included children acutely wheezing with similar inclusion criteria to the asthma-S group with the exception of skin test positivity (skin testing was not performed in this group because it could further deteriorate the acute status of asthma); and 3. Healthy children (control group, N=10) inclusion criteria: a. younger than 18 years of age, b. healthy with no acute infections or major chronic illnesses, and c. negative results to the above-described environmental skin test prick panel. Exclusion criteria to participate in the study included a. 18 years of age or older, b. the use of nasal or systemic steroids within the last 30 days, c. nasal malformations/tumors, and d. acute infectious disease present in the asthma-S or control groups. Children with a concurrent diagnosis of allergic rhinitis were excluded if they had used nasal steroids within 30 days. The use of inhaled steroids was not interrupted for this study. Skin prick testing was performed in the asthma-S and control groups using DermaPiks (Greer Laboratories, Lenoir N.C.). Histamine (1 mg/ml) and normal saline (0.9% NaCl) were used as positive and negative controls. Reactions were considered positive if there was an erythematous base with a wheal ≧3 mm in diameter.

Nasal mucosa sampling was performed using a CytoSoft Brush (Medical Packaging Corp., Camarillo Calif.) and the sample was immediately taken to the laboratory for processing. Samples from children in the group experiencing an asthma exacerbation (asthma-E) were taken within one hour of arrival to the emergency room and before any steroids were given. The cells were suspended in phosphare buffered saline (PBS) and an aliquot was stained with Diff-Quick (Dade Behring Inc, Newark Del.). Cell counting was performed in five high power fields (hpf) and the relative percentages of cell types were calculated. A total eosinophil cell count was also performed.

RNA was isolated from the nasal mucosa sample using TRIZOL according to manufacturer instructions (TRIZOL Reagent, Invitrogen Corporation, Carlsbad Calif.). Average RNA yield was 42.6 µg. In one embodiment, two micrograms of RNA from each subject were pooled to form a group sample containing 20 µg. The three samples (Control, Asthma-S, and Asthma-E) were then submitted to the Affymetrix Genechip Core Facility at Cincinnati Children's Hospital Medical Center for processing and microarray hybridization using the HG-U133A GeneChip (Affymetrix, Santa Clara Calif.) according to Affymetrix guidelines. The HG-U133A chip microarray had a total of 22,215 probe sets (excluding controls) that identified 14,285 genes of which 12,735 are known. In addition, four individual samples from each group (Control, Asthma-S and Asthma-E) were submitted to the Affymetrix Genechip Core Facility at CCHMC for microarray hybridization using the HG-U133_plus 2 GeneChip (Affymetrix) according to Affymetrix guidelines. The HG-U133_plus 2 chip microarray had a total of 54,675 probe sets.

Scanned output files were analyzed using Microarray Suite 5.0 software (Affymetrix). From cell image data files, gene transcript levels were estimated as the Signal strength using the MAS5.0 (Affymetrix). Global scaling was performed to compare genes from chip to chip. Arrays were scaled to the same target intensity value (Tgt=1500) per gene and analyzed independently.

Second-stage data analyses were performed using GeneSpring software (Silicon Genetics, Redwood City Calif.). Initially, data from pooled asthma-S and asthma-E groups were analyzed by looking for genes that were most different in expression relative to the control group sample. A total of 299 cDNAs corresponding to genes that were three-fold up- or down-regulated in the asthma-S or asthma-E groups when compared to the control group were identified. These 299 highly expressed cDNAs were clustered according to their expression profiles along the GI A-P axis by using hierarchical clustering algorithms as implemented in the GeneSpring program. Clustering of the dataset was by several different normalization methods. The use of raw ratios of hybridization versus reference or the log2 of these ratios provided an assessment of genes based on their levels of expression. These 299 highly expressed cDNAs were clustered according to their relative expression profiles using normalization of raw ratios or the log2 of these ratios to the expression of the control group. The number of immune-related genes was obtained for each cluster.

GeneChip data from individual RNA samples were examined by a statistical approach designed to test the hypothesis that genes whose expression was altered in the individual samples would parallel that observed in the pooled samples. Next-generation human HG-U133-plus2 GeneChips (human HG-U133_plus2) were analyzed using MicroArraySuite 5 and the resulting GeneChip intensities were exported to GeneSpring 7.0 and normalized to the median expression level among the four control samples. Genes whose expression varied according to diagnostic group were obtained by first selecting genes that the Affymetrix algorithm reported to be "Present" in at least two gene chips. This returned 32,435 genes from the 54,675 on the chip. Next, an approximately normal distribution of gene expression values was generated by representing each gene's expression as the log of its expression Signal as measured by Microarray Suite. ANOVA was applied to the conditions with a probability of less than 0.01 (acute vs. stable vs. control) to obtain genes differentially expressed between conditions in at least three out of five chips. Each of these lists were further filtered for median expression being at least two-fold different between the two conditions. The resulting gene list of 1378 genes was then subjected to cluster analysis using Standard Correlation as implemented in GeneSpring.

Gene specific primers (designed using Beacon Designer software) were chosen to span at least one intron in the genomic sequence to enable the mRNA-derived product to be distinguished from any possible contaminating genomic product. The sequences of primers for the target genes were as follows: lymphotactin (NM_003175) AATCAAGACCTA-CACCATCAC SEQ ID NO: 1 (sense) and TTCCTGTCCAT-GCTCCTG SEQ ID NO: 2 (anti-sense); histamine 4 (H4) receptor (NM_21624) GGTGTGATCTCCATTCCTTTG SEQ ID NO: 3 (sense) and GCCACCATCAGAGTAA-CAATC SEQ ID NO: 4 (anti-sense); retinoic acid receptor (RARα) (hCT2294851) AGGAGACTGAGATTAGC SEQ ID NO: 5 (sense) and AAGAAGAAGGCGTAGG SEQ ID NO: 6 (anti-sense); CXCL11 (NM_005409) GCTACAGT-TGTTCAAGGCTTCC SEQ ID NO: 7 (sense) and TTGG-GATTTAGGCATCGTTGTC SEQ ID NO: 8 (anti-sense); and ubiquitin C (UBC) (M26880) ATTTGGGTCGCGGT-TCTTGSEQ ID NO: 9 (sense) and TGCCTTGACATTCTC-GATGGT SEQ ID NO: 10 (anti-sense). Prior to cDNA synthesis (using SuperScript U, RNase H, Invitrogen), 1-2 ug of each RNA sample was pretreated with DNase I (Invitrogen) to eliminate any potential contaminating genomic DNA. RT-PCR analysis was conducted with the iCycler (Bio-Rad) using the "iQ SYBR Green Supermix" Taq polymerase mix (Bio-Rad). The amount of double-stranded DNA product, indicated by SYBR Green fluorescence, was measured at the end of each extension cycle. The relative message levels of each target gene were normalized to the UBC housekeeping gene.

Statistical differences between the relative expression levels of RARα, H4R, CXCL11, and lymphotactin genes among the different groups were determined by ANOVA (one-way) of the means and standard error values. This was followed by the Bonferroni procedure to allow for multiple comparisons. A p-value of <0.05 was considered significant.

The mean age in years for the Control (n=10), Asthma-S (n=10), and Asthma-E (n=10) group subjects was 11.7 (SD±2.3), 11.4 (SD±3.4), and 10.1 (SD±6.17) respectively. The gender (male:female) and race (AfricanAmerican:Caucasian) ratios were 7:3 and 8:2 for the control group; 7:3 and 5:5 for the Asthma-S group, and 6:4 and 9:1 for the Asthma-E group. There was no statistical difference between the groups. The children in the asthma-S and asthma-E groups were predominantly African American males, which agreed with published data regarding the racial and gender distributions of childhood asthma in urban environments.

The cellular composition of the nasal respiratory epithelial sample was determined for each subject. For the control group, the average number of cells/hpf (400×) was 265 (SD±104) with 97.7% epithelial cells, 1.84% polymorphonuclear leukocyte cells (PMN), 0.36% squamous cells, and 0.07% eosinophils. For the Asthma-S group the average number of cells/hpf was 219 (SD±87) with 96.3% epithelial cells, 3.32% PMN, 0.30% squamous cells, and 0.09% eosinophils; and for the Asthma-E group the average number of cells/hpf was 154 (SD±69) with 92.3% epithelial cells, 7.24% PMN, 0.18% squamous cells, and 0.25% eosinophils. Epithelial cells represented greater than 92% of the total cells isolated in all groups. There were higher percentages of PMN and eosinophils in samples from children experiencing an asthma exacerbation, however, they remained minor populations (7.2% and 0.25%, respectively) compared with the percentage of respiratory cells (92.3%) and the differences were not statistically significant. Overall, a lower average of total cells was recovered from the nasal samples of children experiencing an asthma exacerbation. While not being bound by a specific theory, this may be due to excessive mucus. RNA was isolated from each sample with an average yield of 42.6 μg per sample from one nostril. Two μg of RNA were pooled from each subject in each group and the three pools were subjected to microarray analysis (HG-U133A Affymetrix GeneChip).

In the asthma-S and asthma-E pooled groups, the expression of 253 (2.0%) of the known genes changed by at least three-fold in either group. The mean raw expression of these genes was 2076 (SD 4322) with a range of 17.4 to 67068 and a median and mode of 1192 and 1903, respectively.

The microarray data are summarized in FIG. 1. Hierarchical clustering and relative expression of genes highly expressed in childhood asthma are shown in panel A. Colors are graded to indicate increased (red) or decreased (blue) expression relative to reference. Relative expression in a given cluster is shown in panel B. The y-axis represents expression normalized to control expression. Cluster analysis examining gene profiles revealed eight distinct clusters of genes regulated in stable and acute childhood asthma. The genes in cluster or group A (N=33) were similarly upregulated in both asthma-S and asthma-E. In cluster B (N=55), genes were upregulated in asthma-S, and further induced in asthma-E. Cluster C genes (N=25) were unchanged in asthma-S, but upregulated in asthma-E. Cluster D genes (N=77) were downregulated in asthma-S, but unchanged in asthma-E. Cluster E genes (N=31) were upregulated in asthma-S, but unchanged in asthma-E. Cluster F genes (N=4) were upregulated in asthma-S, but downregulated in asthma-E. Cluster G genes (N=35) were unchanged in asthma-S, but downregulated in asthma-E. Cluster H genes (N=39) were downregulated in both asthma-S and asthma-E.

Cluster A (N=33), representing genes similarly upregulated in both asthma-S and asthma-E, contained 32 known genes (0.25% of the total known genes). Of these genes, 27.3% were immune-related and 21.2% were involved in signal transduction. The genes in Cluster B that were upregulated during asthma exacerbations (asthma-E) to a higher extent than in asthma-S were comprised of 43.6% immune-related genes. The genes in Cluster C that were upregulated during asthma exacerbations (asthma-E), but unchanged in stable asthma, were comprised of 44% immune-related genes. Clusters D-H were each comprised of less than 6.5% immune-related genes. Genes in Cluster E that were upregulated in children with stable asthma, but unchanged during asthma exacerbations, included 6.5% immune related genes. The genes in this profile included mainly signal transduction genes and cell function enzymes. Clusters D, F, G and H, which contain genes that were downregulated, consist largely of genes involved in basic cell functions and unknown genes.

Distinct clusters of genes that were differentially regulated in childhood asthma were identified, as shown in Tables 1-14.

Distinct sets of genes were activated during stable vs. exacerbated asthma, establishing that exacerbated asthma status is distinguished based on the occurrence of strong gene expression signatures in nasal epithelial samples. Stable asthma status also exhibited differential signatures but with more variability. While not bound by any theory, this may suggest clinical and or mechanistic heterogeneity among the patients.

In the exacerbated asthma pooled sample, 12 genes were upregulated at least two-fold (Table 15) and 50 genes were upregulated at least three-fold (Table 16) as compared to the control pooled sample. Fourteen genes in the exacerbated asthma pooled sample were downregulated by at least two-fold (Table 17) and 7 genes were downregulated by at least three-fold (Table 18), compared to the control pooled sample. In the stable asthma pooled sample, 7 genes were upregulated by at least two-fold (Table 19) and 11 genes were upregulated by at least three-fold (Table 20) compared to the control pooled sample. Also, 6 genes in the stable asthma pooled sample were downregulated by at least two-fold (Table 21) and 4 genes were downregulated by at least three-fold (Table 22) compared to the control pooled sample.

Reverse transcription polymerase chain reaction (RT-PCR) analysis confirmed expression of genes identified by microarray. For the microarray analysis, equivalent amounts of RNA were pooled from individuals in each group. All individual RNA samples isolated from nasal mucosal cells from participants from the control (N=10), asthma-S(N=10), and asthma-E (N=10) groups were analyzed by RT-PCR for expression of each gene. Four genes (CXCL11, RARα, H4R, and lymphotactin) were examined: one induced in the asthma-E group exclusively (Cluster C), one induced in the asthma-S group exclusively (Cluster E), and two simultaneously induced in both groups (Cluster A).

Quantitative RT-PCR analysis is shown in FIG. 2, with the y-axis in each graph representing relative message levels, normalized to the average of duplicate UBC message levels. RT-PCR confirmed increased expression of the selected genes in asthma-S and/or asthma-E. CXCL11 expression was increased in asthma-E to a greater extent than asthma-S. RARα was induced in asthma-S, but not asthma-E, and lymphotactin was induced equally in asthma-S and asthma-E. The RT-PCR data validated the genes identified by chip array and confirmed differential expression in the asthma-E and asthma-S groups.

FIG. 3 shows hierarchical clustering of genes highly expressed in individual children with stable and exacerbated asthma compared with controls, with colors graded to indicate increased (red) or decreased (blue) expression relative to reference. The clustering results from the individual samples are presented beside the data from the RNA samples pooled from each group (N=10). As shown, the data from the individual samples were substantially consistent both between individuals and when compared to the pooled sample data. A stepwise filtering method was used to derive a total of 161 genes whose expression was significantly different between the groups (ANOVA, p<0.01), and in addition was of sufficient magnitude to increase or decrease by at least two-fold in 3 of the 4 individual samples.

In the exacerbated asthma individual group (versus the pooled group), 88 genes were upregulated and 53 genes were downregulated compared to the control group. In the stable asthma group, 21 genes were upregulated and 12 genes were downregulated. More specifically, in the exacerbated asthma group, 9 genes exhibited at least a two-fold increase (Table 1) and 79 genes showed at least a three-fold increase (Table 2) compared to controls. Also, 36 genes were decreased by at least two-fold (Table 3) and 15 genes were decreased by at least three-fold (Table 4) compared to controls. In the stable asthma group, 11 genes were upregulated by at least two-fold (Table 5) and 10 genes were upregulated by at least three-fold (Table 6) compared to controls. Also, 8 genes were downregulated by at least two-fold (Table 7) and 4 genes were downregulated by at least three-fold (Table 8) compared to controls. Many of the changes in gene expression were specific to either stable or exacerbated asthma in that gene expression did not change in the other group or had the opposite change in expression. For example, 70 genes that exhibited at least a two-fold increase in the exacerbated asthma group showed no change of expression in the stable asthma group (Table 9). Also, 50 genes were downregulated by at least two-fold in the exacerbated asthma group but were unchanged in the stable asthma group (Table 10). For stable asthma specific genes, 4 genes were upregulated by at least two-fold while unchanged in the exacerbated asthma group (Table 11) and 9 genes were downregulated by at least two-fold in the stable asthma group and remained unchanged in the exacerbated asthma group (Table 12). In some cases, the direction of change in gene expression was the same for both the stable and exacerbated asthma groups. For example, 16 genes showed at least a two-fold increase in expression in both groups compared to control groups (Table 13). Four genes exhibited an inverse in expression levels, with a gene upregulated by at least two-fold in the exacerbated asthma group and downregulated by at least two-fold in the stable asthma group, or vice versa (Table 14).

Figure 4B:
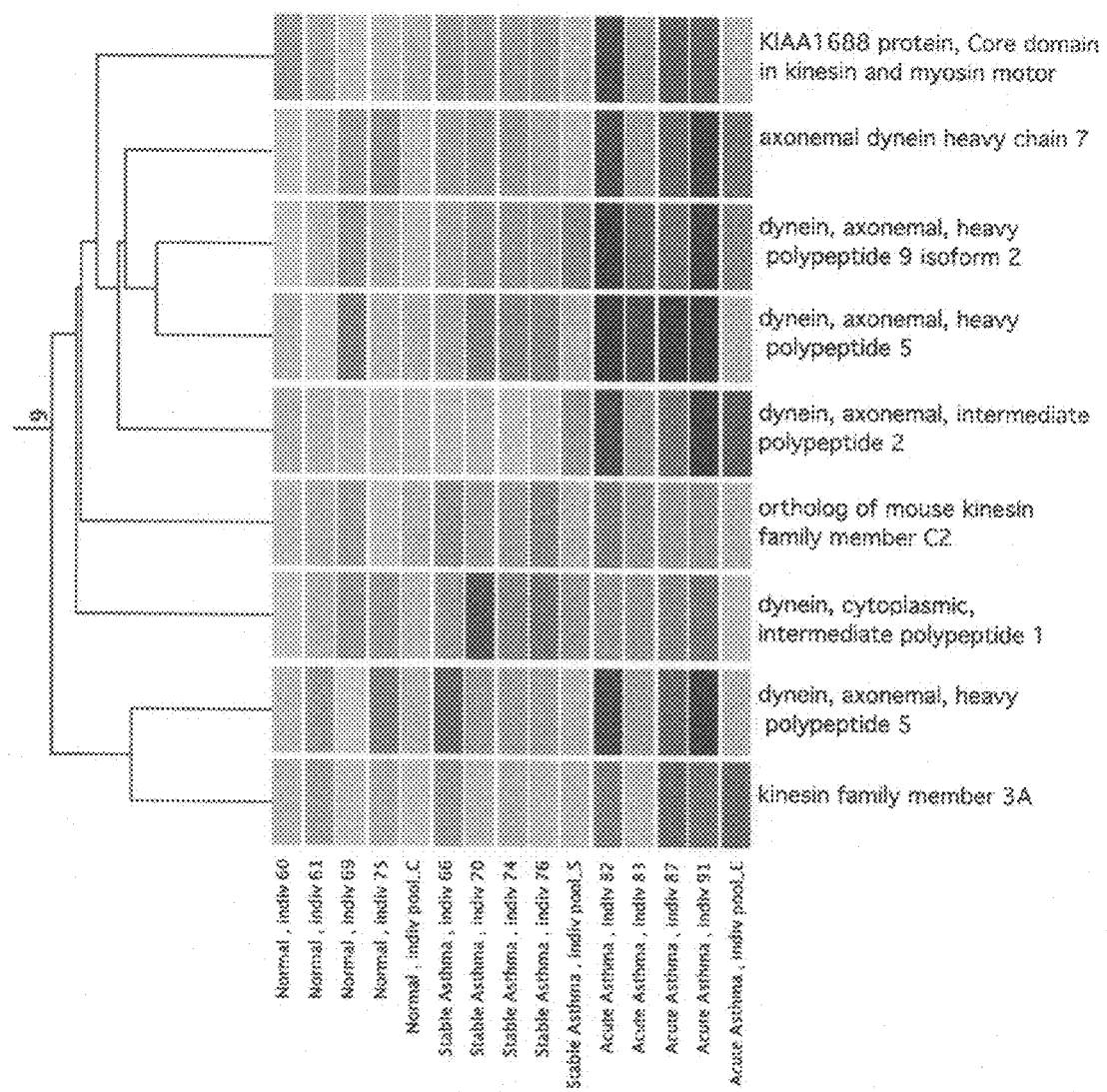

Among the 161 most upregulated and downregulated genes (at least three-fold change, p<0.01) that were consistent in at least 3 of the 4 samples, classes of genes were evaluated to determine if a particular class of genes was overrepresented. Two classes of genes were noted as shown in FIG. 4. Selected upregulated immune-related genes (A) and downregulated cilia-related genes (B) compared with controls in at least 3 out of 4 samples. Among the upregulated genes, 37 immune-related genes were consistently upregulated at least three-fold (FIG. 4A). Among the downregulated genes, 9 cilia-related genes were consistently downregulated at least three-fold (FIG. 4B).

Respiratory epithelial cells serve as an accessible alternative proxy for lower respiratory epithelium, even if they may not fully represent the genes that are expressed in the lungs of children with asthma. Many of the genes that were found to be induced in childhood asthma have been implicated in the pathogenesis of asthma in other studies, including arginase, SOCS-3, complement 3a receptor, and lymphotactin. For the chip array analysis, both pooled samples derived from equivalent amounts of RNA from each individual in each group, as well as individual samples, were utilized. The gene expression signatures obtained from the individual samples agreed with the pooled samples. RT-PCR of the individual RNA samples further validated findings and RT-PCR confirmed the chip array data.

The percentage of immune related genes was examined in each cluster. In the pooled samples, clusters that included genes induced specifically in either asthma exacerbations (Cluster C) or genes that were induced at a higher level during asthma exacerbations (Cluster D) contained the highest percentages and absolute numbers of immune-related genes. This was confirmed by further chip array analyses of the individual samples. The immune-related genes were overrepresented among the most upregulated genes. Genes that are not classified as immune genes may have direct or indirect effects on the immune system. Asthma-E samples demonstrated the strongest and most reproducible signatures and these signatures were distinct from Asthma-S. Among the most downregulated genes, cilia-related genes were overrepresented. Because the respiratory epithelium is often damaged in asthma and there is an overproduction of mucus, one might predict that genes important in ciliary function would be induced. While not being bound by any theory, downregulation in cilia-related genes may contribute to asthma pathogenesis by impairing mucus clearance. Alternatively, downregulation of cilia genes may be a response to damage and may be used for repair or remodeling.

Each cluster identifies novel potential target candidate genes for childhood asthma. In Cluster A, the H4 receptor gene was induced nearly ten-fold. This gene was recently cloned and found to be expressed in leukocytes, including eosinophils, as well as the lung and it is involved in childhood asthma. In contrast, the H1, H2, and H3 receptors were not induced. Also in Cluster A, SOCS-3 was induced nearly ninefold. SOCS-3 expression correlates strongly with the pathology of asthma and atopic dermatitis, as well as serum IgE levels in allergic human patients. The complement 3α receptor 1 gene SEQ ID NO: 65 in Table 2 was induced. In a previous study examining the role of C3α in asthma, C3α levels were increased following segmental airway challenge in sensitized adults with asthma, and the receptor is also regulated during the effector phase of asthma. Several IFN-induced proteins were also induced in this cluster of genes induced in asthma-E to a greater level than asthma-S. Because asthma exacerbations in children can be associated with upper respiratory viral infections, some of these may represent an IFN-mediated anti-viral response. Genes that were induced exclusively during asthma exacerbations (Table 9) included integrin α4 as well as several chemokines and chemokine receptors. Integrin α4 (CD49d), which is important for eosinophil survival and recruitment, was induced 8.6 fold in children experiencing asthma exacerbation, but not in children with stable asthma. In contrast, genes that were induced in asthma-S, but not asthma-E (Table 11) did not include chemokine receptors nor chemokines. The most strongly induced gene in this cluster was the gene encoding RARα, which was induced approximately 28-fold compared to non-asthmatic children. Retinoids exert multiple effects upon lung differentiation and growth, and this receptor may contribute to lung repair or remodeling in children with ongoing stable asthma. Another gene in this cluster is arginase, supporting its roles as a mediator of childhood asthma. In a recent study, adults with stable asthma had increased arginase expression in their lungs and BALF compared with normal controls. In a previous study utilizing microarray analysis to identify genes important in asthma RNA isolated from peripheral blood mononuclear cells from adults with atopic asthma, allergic rhinitis but not asthma, and healthy controls was analyzed. Decreased levels of interferon α/β receptor (ratio 0.42) were found, similar to results in Cluster H.

Although environmental factors likely contribute to the different prevalence rates, genes with large allele frequency differences between a Caucasian population and a Han Chinese population may be partly responsible for the current variation in asthma susceptibility. One-hundred and sixty-one known genes identified by microarray data were examined for large allele frequency differences between Caucasian and Han Chinese populations. Allele frequencies of the single nucleotide polymorphisms (SNPs) within each gene in Caucasians and in Han Chinese were retrieved from the public HapMap database (http://www.hapmap.org). $F_{ST}$ was calculated as $F_{ST}=\sigma^2/pq$, where $\sigma^2$ is the variance in allele frequency, and p and q are the average allele frequency of each allele among subpopulations, respectively. When comparing two subpopulations with two alleles in each, the variance in allele frequency equals to $\sigma^2=(p_1-p_2)^2/4$, where $p_1$ is the allele frequency in the first subpopulation, and $p_2$ is the frequency of the same allele in the second subpopulation. Therefore, the $F_{ST}$ was calculated by $F_{ST}=(p_1-p_2)^2/(4p(1-p))$. The sample size obtained from HapMap project was large, i.e., 60 and 45 unrelated Caucasians and Han Chinese were genotyped, respectively, and allowed for calculation of $F_{ST}$ without additional corrections. $F_{ST}$ has a theoretical minimum of 0, indicating no genetic divergence, and a theoretical maximum of 1, indicating fixation for alternative alleles in different subpopulations. The observed $F_{ST}$ is usually much less than 1 in human subpopulations. The following qualitative guidelines were used for the interpretation of $F_{ST}$: $0<F_{ST}<0.05$: little genetic differentiation; $0.05<F_{ST}<0.15$: moderate genetic differentiation; $0.15<F_{ST}<0.25$: great genetic differentiation; and $F_{ST}>0.25$: very great genetic differentiation.

The $F_{ST}$ for each identified SNPs (from HapMap database) was calculated in each of the 161 most regulated genes related to childhood asthma based on the gene expression profile comparisons. Among the asthma signature genes from the chip array results, there were 43 genes (39%) with large allele frequency differences ($F_{ST}>0.15$) between Caucasian and Han Chinese populations. Of these 43 genes, 17 had a $F_{ST}>0.25$ (Table 23) and 26 had a $0.15>F_{ST}>0.25$ (Table 24). This proportion is higher than the average genetic differentiation between these two subpopulations.

Among these 43 genes, six genes (PDE4B SEQ. ID NO. 27; SPRR2B SEQ. ID NO. 109; ADCY2 SEQ. ID NO. 46; KIF3A SEQ. ID NO. 80; DNAH5 SEQ ID NO. 115; and PLAUSEQ. ID NO. 98) are located in chromosomal regions that have been linked to asthma phenotypes and atopy phenotypes and have been shown to either be regulated during allergic inflammation and/or to regulate release of Th2 cytokines including IL-13. These six genes have been shown to either be regulated during allergic inflammation and/or to regulate release of Th2 cytokines including IL-13. The following summarizes of each gene and its relationship to allergic inflammation and IL-13.

Phosphodiesterase 4B (PDE4B): The cyclic nucleotides, cAMP and cGMP, are important second messengers known to control many cellular processes. In inflammatory cells, activation of cAMP signaling has negative modulatory effects on numerous steps required for immune inflammatory responses, including T cell activation and proliferation, cytokine recruitment and recruitment of leukocyte. The cyclic nucleotide signaling system is complex and interlinked with many other pathways. Their signals are tightly controlled by regulating the synthesis and breakdown of these molecules. Phosphodiesterases are the enzymes that degrade and inactivate cyclic nucleotides. The phosphodiesterase 4 (PDE4) family consists of four genes (PDE4A-D) and each gene encodes multiple variants generated from alternate splicing and different transcriptional promoters. The phenotypes of the different PDE4 null mice support unique functions for each PDE4 gene. PDE4B null mice are generally healthy, but peripheral blood leukocytes derived from PDE4B null mice produce very little TNFα in response to LPS. Extensive studies using specific PDE4B inhibitors both in vitro and in vivo have demonstrated a potent anti-inflammatory effect as well as regulation of airway smooth muscle by PDE4B. Given the broad inhibitory effects, pharmacologic manipulation of PDE4 is a promising approach for treating chronic inflammatory conditions including asthma. In animal models of asthma, PDE4 inhibitors have been shown to inhibit airway inflammation and remodeling. A key feature of chronic inflammatory airway diseases such as asthma is mucus hypersecretion. MUC5AC is the predominant mucin gene expressed in healthy airways and is increased in asthmatic patients. Selective PDE4 inhibition was shown to be effective in decreasing EGF-induced MUC5AC expression in human airway epithelial cells. In a placebo-controlled, randomized clinical trial, PDE4 inhibition was found to be efficacious in exercise-induced asthma; the mean percentage fall of FEV1 after exercise was reduced by 41% as compared to placebo.

One mechanism by which PDE4 inhibitors exert an anti-inflammatory effect is by inhibiting IL-13 production in allergic diseases by T cells and basophils. In one study, phytohaemagglutinin (PHA)-induced IL-13 release from peripheral blood mononuclear cells from atopic asthma patients was inhibited by rolipram, a PDE4 inhibitor. In another study, rolipram inhibited IL-13 production from PHA- or anti-CD3 plus anti-CD28-stimulated human T cells. Similarly, PDE4 inhibition blocked *Dermatophagoides pteronyssinus*-induced interleukin-13 secretion in atopic dermatitis T cells.

Small proline-rich protein 2B (SPRR2B): SPRR genes encode a class of small proline rich proteins that are strongly induced during differentiation of human epidermal keratinocytes in vitro and in vivo. They are encoded by closely related members of a gene family closely linked within a 300-kb DNA segment on human chromosome 1q21-q22 in a region that has been linked to atopy phenotypes. These genes are expressed predominantly in squamous epithelium, where they contribute to the formation of the insoluble cornified crosslinked envelope that provides structural integrity and limits permeability through transglutaminase-induced N-glutamyl)lysine isopeptide crosslinks and interchain disulfide bonds. Studies using primary human and murine cells grown at the air-liquid interface demonstrated that IL-13 directly induces SPRR2B. In fact SPRR2B was one of only four genes that was induced more strongly by IL-13 than IL-4. The fact that SPRR2B was strongly induced by IL-13 supported that it may be important in the pathogenesis of allergic disease. This role for SPRR2b substantiated in a recent study by Drs. Rothenberg and Wills-Karp where SPRR2B was shown to be induced in lungs of mice in a mouse model of asthma in a Stat6-dependent fashion. Thus, SPRR2 is an allergen- and IL-13-induced gene in experimental allergic responses that may be involved in disease pathophysiology.

Adenylate Cyclase 2 (ADCY2): This gene encodes a member of the family of adenylate cyclases, which are membrane-associated enzymes that catalyze the formation of the secondary messenger cyclic adenosine monophosphate (cAMP). This enzyme is insensitive to Ca(2+)/calmodulin, and is stimulated by the G protein beta and gamma subunit complex. It is located on chromosome 5p15 in a region that has been linked to atopy phenotypes. Cyclic AMP has a broad range of anti-inflammatory effects on a variety of effector cells involved in asthma. Pharmacologic inhibition of adenylate cyclases inhibited IL-13 production from PHA- or anti-CD3 plus anti-CD28-stimulated human T cells.

Kinesin family member 3A (KIF3A): KIF3 is a heterotrimeric member of the kinesin superfamily of microtubule associated motors. This functionally diverse family of proteins mediates transport between the endoplasmic reticulum and the Golgi, transports protein complexes within cilia and flagella, and is involved in anterograde transport of membrane bound organelles in neurons and melanosomes. Embryos lacking KIF3A die at 10 days postcoitum, exhibit randomized establishment of L-R asymmetry, and display numerous structural abnormalities. Interestingly, the KIF3A gene is located on 5q31 in a region that has demonstrated linkage to asthma and atopy in multiple studies. It is located immediately upstream of IL4 and IL13 and conserved non-coding sequences in this area have been implicated in the coordinate transcriptional regulation of IL-4 and IL-13.

Dynein, axonemal, heavy polypeptide 5 (DNAH5): DNAH5 is a component of the outer dynein arm of cilia. Mutations in DNAH5 resulting in non-functional proteins have been found to be responsible for primary ciliary dyskinesia. Similar to ADCY2, the DNAH5 gene is located on chromosome 5p15 in a region that has been linked to atopy phenotypes. IL-13 has direct effects on ciliary function, specifically it alters mucociliary differentiation and decreases ciliary beat frequency of ciliated epithelial cells.

Plasminogen activator, urokinase (PLAU): PLAU is located on chromosome 10q24 and its gene product, urokinase, is serine protease involved in degradation of the extracellular matrix. Urokinase converts plasminogen to plasmin by specific cleavage of an Arg-Val bond in plasminogen. Recent studies suggest that the plasmin system plays an active role in tissue remodeling by influencing the production of inflammatory mediators and growth factors. Plasmin also degrades the extracellular matrix (ECM), either directly removing glycoproteins from ECM or by activating matrix metalloproteinases (MMPs). Urokinase is synthesized by airway cells, and inflammatory mediators affect its expression. In mouse models of asthma urokinase is induced in the lungs of mice, and in monocytes urokinase is induced in response to IL-4 and IL-13. The role of urokinase in inflammation was further defined in a recent study whereby urokinase gene-targeted mice fail to generate a Th2 immune response following schistosomal antigen challenge. The plasmin system is also involved in eotaxin-mediated chemotaxis of eosinophils.

Each of the gene products is expressed in respiratory epithelium. None of these epithelial genes have been studied as potential candidate genes for asthma.

In summary, the distinct gene expression profiles in nasal respiratory epithelial cells of children with stable asthma (asthma-S) and children experiencing an asthma exacerbation (asthma-E) provided an overview of the genetic portrait of childhood asthma and the differences in genes important in promoting the development of asthma versus promoting the ongoing phenotype of asthma. Strong gene expression signatures that reflect clinical asthma attack status in readily sampled patient tissues provide a new opportunity for molecular sub-classification and clinical management of asthma patients. Both stabilized and acutely affected asthmatic children exhibited characteristic expression profiles that affect understanding of disease status, treatment response, and new therapies.

TABLE 1

Individual samples
Exacerbated Asthma two-fold increase

| Common | Description | Genbank | Seq. ID Number |
|---|---|---|---|
| EMR2 | egf-like module containing, mucin-like, hormone receptor-like 2 | NM_013447 | 22 |
| THBD | thrombomodulin | NM_000361 | 23 |
| ZNF407 | zinc finger protein 407 | NM_017757 | 31 |
| ALDH1A3 | aldehyde dehydrogenase 1 family, member A3 | NM_000693 | 39 |
| OLR1 | oxidized low density lipoprotein (lectin-like) receptor 1 | NM_002543 | 69 |
| SCEL | sciellin | NM_144777 | 77 |
| PLAU | plasminogen activator, urokinase | NM_002658 | 98 |
| DCP2 | decapping enzyme hDcp2 | NM_152624 | 126 |
| SLC30A7 | solute carrier family 30 (zinc transporter), member 7 | NM_133496 | 152 |

TABLE 2

Individual samples
Exacerbated Asthma three-fold increase

| Common | Description | Genbank | Seq. ID Number |
|---|---|---|---|
| KRT24 | keratin 24 | NM_019016 | 14 |
| SOSTDC1 | sclerostin domain containing 1 | NM_015464 | 15 |
| BM039 | uncharacterized bone marrow protein BM039 | NM_018455 | 16 |
| KRT6A | keratin 6A | NM_005554 | 17 |
| CALB1 | calbindin 1, 28 kDa | NM_004929 | 18 |
| GPR65 | G protein-coupled receptor 65 | NM_003608 | 20 |
| FPRL1 | formyl peptide receptor-like 1 | NM_001462 | 24 |
| PROK2 | prokineticin 2 | NM_021935 | 26 |
| PDE4B | phosphodiesterase 4B, cAMP-specific (phosphodiesterase E4 dunce homolog, *Drosophila*) | NM_002600 | 27 |
| FOS | v-fos FBJ murine osteosarcoma viral oncogene homolog | NM_005252 | 28 |
| TREM1 | triggering receptor expressed on myeloid cells 1 | NM_018643 | 29 |
| HAL | histidine ammonia-lyase | NM_002108 | 30 |
| SLC2A14 | solute carrier family 2 (facilitated glucose transporter), member 14 | NM_153449 | 32 |
| AQP9 | aquaporin 9 | NM_020980 | 33 |
| BCL2A1 | BCL2-related protein A1 | NM_004049 | 34 |
| CYP1A1 | cytochrome P450, family 1, subfamily A, polypeptide 1 | NM_000499 | 35 |
| SERPINB4 | serine (or cysteine) proteinase inhibitor, clade B (ovalbumin), member 4 | NM_002974 | 36 |

TABLE 2-continued

Individual samples
Exacerbated Asthma three-fold increase

| Common | Description | Genbank | Seq. ID Number |
|---|---|---|---|
| CLECSF6 | C-type (calcium dependent, carbohydrate-recognition domain) lectin, superfamily member 6 | NM_016184 | 40 |
| IL1B | interleukin 1, beta | NM_000576 | 41 |
| LILRB1 | leukocyte immunoglobulin-like receptor, subfamily B (with TM and ITIM domains), member 1 | NM_D06669 | 42 |
| SLC2A3 | solute carrier family 2 (facilitated glucose transporter), member 3 | NM_006931 | 43 |
| S100A9 | S100 calcium binding protein A9 (calgranulin B) | NM_002965 | 44 |
| PLEK | pleckstrin | NM_002664 | 45 |
| DTNA | dystrobrevin, alpha | NM_001390 | 47 |
| ARNTL2 | aryl hydrocarbon receptor nuclear translocator-like 2 | NM_020183 | 48 |
| RAI3 | retinoic acid induced 3 | NM_003979 | 49 |
| G0S2 | putative lymphocyte G0/G1 switch gene | NM_015714 | 50 |
| RPEL1 | RPEL repeat containing 1 | AB051520 | 51 |
| CSF2RB | colony stimulating factor 2 receptor, beta, low-affinity (granulocyte-macrophage) | NM_000395 | 52 |
| PLAUR | plasminogen activator, urokinase receptor | NM_002659 | 53 |
| HIST1H2BH | histone 1, H2bh | NM_003524 | 54 |
| EMP1 | epithelial membrane protein 1 | NM_001423 | 55 |
| TF | transferrin | NM_001063 | 56 |
| PRG1 | proteoglycan 1, secretory granule | NM_002727 | 57 |
|  | unnamed protein product; diaminopimelate decarboxylase (AA 1-327); *Bacillus subtilis* lys gene for diaminopimelate decarboxylase (EC 4.1.1.20). | X17013 | 58 |
| PLEK | pleckstrin | NM_002664 | 59 |
| GPR43 | G protein-coupled receptor 43 | NM_005306 | 60 |
| HIST1H2BC | histone 1, H2bc | NM_003526 | 61 |
| SPRR1A | small proline-rich protein 1A | NM_005987 | 62 |
| ITGAM | integrin, alpha M (complement component receptor 3, alpha; also known as CD11b (p170), macrophage antigen alpha polypeptide) | NM_000632 | 65 |
| SOD2 | superoxide dismutase 2, mitochondrial | NM_000636 | 67 |
| GPR97 | G protein-coupled receptor 97 | NM_170776 | 70 |
| SPEC1 | small protein effector 1 of Cdc42 | NM_020239 | 72 |
| MMP25 | matrix metalloproteinase 25 | NM_022468 | 73 |
| AKR1B10 | synonyms: HIS, HSI, ARL1, ARL-1, ALDRLn, AKR1B11, AKR1B12, MGC14103; aldose reductase-like 1; aldo-keto reductase family 1, member B11 (aldose reductase-like); aldose reductase-like peptide; aldose reductase-related protein; small intestine reductase; go_ | NM_004812 | 74 |
| AKR1B10 | synonyms: HIS, HSI, ARL1, ARL-1, ALDRLn, AKR1B11, AKR1B12, MGC14103; aldose reductase-like 1; aldo-keto reductase family 1, member B11 (aldose reductase-like); aldose reductase-like peptide; aldose reductase-related protein; small intestine reductase; go_ | NM_020299 | 75 |
| EMP1 | epithelial membrane protein 1 | NM_001423 | 76 |
| HM74 | putative chemokine receptor | NM_006018 | 78 |
| NR4A1 | nuclear receptor subfamily 4, group A, member 1 | NM_002135 | 79 |
| HIST1H1C | histone 1, H1c | NM_005319 | 83 |
|  | *Homo sapiens* transcribed sequences | BQ010718 | 84 |
| SERPINB13 | serine (or cysteine) proteinase inhibitor, clade B (ovalbumin), member 13 | NM_012397 | 86 |
| HIST1H2BK | histone 1, H2bk | NM_080593 | 88 |
| IL1R2 | interleukin 1 receptor, type II | NM_004633 | 90 |
| DUSP5 | dual specificity phosphatase 5 | NM_004419 | 92 |
| TLR4 | toll-like receptor 4 | NM_003266 | 93 |
| CCR1 | chemokine (C—C motif) receptor 1 | NM_001295 | 94 |
| RAI3 | retinoic acid induced 3 | NM_003979 | 96 |
| KRT13 | keratin 13 | NM_153490 | 97 |
|  | *Homo sapiens* transcribed sequences | BQ277484 | 101 |
| SLC11A1 | solute carrier family 11 (proton-coupled divalent metal ion transporters), member 1 | NM_000578 | 105 |
| C1QR1 | complement component 1, q subcomponent, receptor 1 | NM_012072 | 106 |
| IL1A | interleukin 1, alpha | NM_000575 | 107 |
| SPRR2B | small proline-rich protein 2B | NM_001017418 | 109 |
| SPRR3 | small proline-rich protein 3 | NM_005416 | 110 |
| MAD | MAX dimerization protein 1 | NM_002357 | 112 |
| CLECSF12 | C-type (calcium dependent, carbohydrate-recognition domain) lectin, super-family member 12 | NM_197953 | 114 |
| SPRR1B | small proline-rich protein 1B (cornifin) | NM_003125 | 117 |
| EAT2 | SH2 domain-containing molecule EAT2 | NM_053282 | 120 |
| PRV1 | polycythemia rubra vera 1 | NM_020406 | 129 |
| RAB35 | RAB35, member RAS oncogene family | NM_006861 | 132 |
| S100A2 | S100 calcium binding protein A2 | NM_005978 | 134 |

TABLE 2-continued

Individual samples
Exacerbated Asthma three-fold increase

| Common | Description | Genbank | Seq. ID Number |
|---|---|---|---|
| CD44 | CD44 antigen (homing function and Indian blood group system) | NM_000610 | 135 |
| JUNB | jun B proto-oncogene | NM_002229 | 139 |
| LILRB2 | leukocyte immunoglobulin-like receptor, subfamily B (with TM and ITIM domains), member 2 | NM_005874 | 145 |
| C4.4A | GPI-anchored metastasis-associated protein homolog | NM_014400 | 146 |
| CPA4 | carboxypeptidase A4 | NM_016352 | 153 |
| LILRB1 | leukocyte immunoglobulin-like receptor, subfamily B (with TM and ITIM domains), member 1 | NM_006669 | 160 |
| FCGR2A | Fc fragment of IgG, low affinity IIa, receptor for (CD32) | NM_021642 | 163 |

* Denotes a "corrected" accession number found in Genbank

TABLE 3

Individual samples
Exacerbated Asthma two-fold decrease

| Common | Description | Genbank | Seq. ID Number |
|---|---|---|---|
| SF1 | splicing factor 1 | NM_004630 | 11 |
| KCTD7 | potassium channel tetramerisation domain containing 7 | NM_153033 | 12 |
| DNAH7 | dynein, axonemal, heavy polypeptide 7 | NM_018897 | 63 |
| FLJ23505 | *Homo sapiens* cDNA: FLJ23505 fis, clone LNG03017 | NM_024716 | 68 |
| KIF3A | kinesin family member 3A | NM_007054 | 80 |
| IGFBP7 | insulin-like growth factor binding protein 7 | NM_001553 | 81 |
| TSAP6 | tumor suppressor pHyde; *Homo sapiens* dudulin 2 (TSAP6), mRNA. | NM_182915 | 82 |
| IPW | *Homo sapiens* mRNA; cDNA DKFZp686M12165 (from clone DKFZp686M12165) | BX648788 | 89 |
| PLTP | phospholipid transfer protein | NM_006227 | 91 |
|  | gb: BC029442.1/DB_XREF = gi: 20809535/TID = Hs2Affx.1.373/CNT = 1/FEA = FLmRNA/TIER = FL/STK = 1/ NOTE = sequence(s) not in UniGene/DEF = *Homo sapiens*, Similar to immunity associated protein 1, clone MGC: 32707 IMAGE: 4618467, mRNA, complete cds./PROD = Similar to immu | BC029442 | 99 |
| SIAH1 | seven in absentia homolog 1 (*Drosophila*) | NM_003031 | 100 |
|  | *Homo sapiens* transcribed sequences | BX107340 | 103 |
| FLJ40427 | hypothetical protein FLJ40427 | NM_178504 | 108 |
| DNAH5 | dynein, axonemal, heavy polypeptide 5 | NM_001369 | 115 |
| DNAH9 | dynein, axonemal, heavy polypeptide 9 | NM_001372 | 116 |
|  | *Homo sapiens* cDNA FLJ12411 fis, clone MAMMA1002964. | AK022473 | 118 |
| LOC123872 | similar to RIKEN cDNA 4930457P18 | NM_178452 | 121 |
| CHST5 | carbohydrate (N-acetylglucosamine 6-O) sulfotransferase 5 | NM_024533 | 122 |
|  | UI-H-BW0-aim-d-12-0-UI.s1 NCI_CGAP_Sub6 *Homo sapiens* cDNA clone IMAGE: 2729902 3', mRNA sequence. | AW294722 | 123 |
| KIAA1688 | KIAA1688 protein | AB051475 | 125 |
| DCDC2 | doublecortin domain containing 2 | NM_016356 | 127 |
|  | *Homo sapiens* transcribed sequences | CD698727 | 128 |
| SPAG8 | sperm associated antigen 8 | NM_012436 | 130 |
| ATM | ataxia telangiectasia mutated (includes complementation groups A, C and D) | NM_000051 | 138 |
| FLJ13621 | hypothetical protein FLJ13621 | NM_025009 | 140 |
| HPX | hemopexin | NM_000613 | 141 |
| DNAI2 | dynein, axonemal, intermediate polypeptide 2 | NM_023036 | 143 |
|  | *Homo sapiens* mRNA; cDNA DKFZp761D2417 (from clone DKFZp761D2417) | AL831856 | 148 |
|  |  |  | 148 |
| MGC16202 | hypothetical protein MGC16202 | NM_032373 | 156 |
|  | *Homo sapiens* LOH11CR1P gene, loss of heterozygosity, 11, chromosomal region 1 gene P product | CA428747 | 157 |
| LOC146177 | *Homo sapiens* hypothetical protein LOC146177 (LOC146177), mRNA. | NM_175059 | 158 |
| MGC40053 | hypothetical protein MGC40053 | NM_152583 | 161 |
| LOC339005 | *Homo sapiens* cDNA FLJ33935 fis, clone CTONG2017910. | AK091254 | 162 |
| C18orf1 | alternatively spliced; beta-1 form; possible membrane-spanning protein; clone 22; *Homo sapiens* chromosome 18 open reading frame 1 (C18orf1), mRNA. | NM_181481 | 164 |
| MYEF2 | myelin expression factor 2 | NM_016132 | 165 |
| DNAH3 | dynein, axonemal, heavy polypeptide 3 | NM_017539 | 167 |

TABLE 4

Individual samples
Exacerbated Asthma three-fold decrease

| Common | Description | Genbank | Seq. ID Number |
|---|---|---|---|
| CLGN | calmegin | NM_004362 | 13 |
| ADCY2 | adenylate cyclase 2 (brain) | NM_020546 | 46 |
|  | *Homo sapiens* transcribed sequence with weak similarity to protein sp: P39194 (*H. sapiens*) ALU7_HUMAN Alu subfamily SQ sequence contamination warning entry | BX361062 | 66 |
| MGC26733 | hypothetical protein MGC26733 | NM_144992 | 104 |
| MYLK | myosin, light polypeptide kinase | NM_053025 | 111 |
| SLC26A7 | solute carrier family 26, member 7 | NM_052832 | 119 |
|  | *Homo sapiens* cDNA: FLJ22631 fis, clone HSI06451. | AK026284 | 124 |
| LOC138428 | hypothetical protein LOC286207 | AL833241 | 133 |
|  | *Homo sapiens* cDNA: FLJ22781 fis, clone KAIA1958. | AK026434 | 136 |
|  | *Homo sapiens* cDNA FLJ12093 fis, clone HEMBB1002603. | AK022155 | 137 |
|  | *Homo sapiens* cDNA: FLJ23502 fis, clone LNG02862 | AK027155 | 142 |
| LOC165186 | UI-H-EZ1-bbk-j-02-0-UI.s1 NCI_CGAP_Ch2 *Homo sapiens* cDNA clone UI-H-EZ1-bbk-j-02-0-UI 3', mRNA sequence.; ESTs, Weakly similar to T00057 hypothetical protein KIAA0423 - human (fragment) [*H. sapiens*] | NM_199280 | 144 |
|  | UI-E-EJ0-ahi-c-20-0-UI.r1 UI-E-EJ0 *Homo sapiens* cDNA clone UI-E-EJ0-ahi-c-20-0-UI 5', mRNA sequence. | BM712946 | 149 |
| FLJ14665 | Start codon is not identified.; *Homo sapiens* mRNA for KIAA1864 protein, partial cds. | AB058767 | 155 |
| SCARF2 | scavenger receptor class F, member 2 | NM_153334 | 159 |

TABLE 5

Individual samples
Stable Asthma two-fold increase

| Common | Description | Genbank | Seq. ID Number |
|---|---|---|---|
| SOSTDC1 | sclerostin domain containing 1 | NM_015464 | 15 |
| BM039 | uncharacterized bone marrow protein BM039 | NM_018455 | 16 |
| CALB1 | calbindin 1, 28 kDa | NM_004929 | 18 |
| CYP1A1 | cytochrome P450, family 1, subfamily A, polypeptide 1 | NM_000499 | 35 |
|  | *Homo sapiens* transcribed sequences | AI476722 | 37 |
| EMP1 | epithelial membrane protein 1 | NM_001423 | 76 |
| SCEL | sciellin | NM_144777 | 77 |
|  | UI-H-BW0-aim-d-12-0-UI.s1 NCI_CGAP_Sub6 *Homo sapiens* cDNA clone IMAGE: 2729902 3', mRNA sequence. | AW294722 | 123 |
| DCP2 | decapping enzyme hDcp2 | NM_152624 | 126 |
| RAB35 | RAB35, member RAS oncogene family | NM_006861 | 132 |
| SLC30A7 | solute carrier family 30 (zinc transporter), member 7 | NM_133496 | 152 |

TABLE 6

Individual samples
Stable Asthma three-fold increase

| Common | Description | Genbank | Seq. ID Number |
|---|---|---|---|
| FOS | v-fos FBJ murine osteosarcoma viral oncogene homolog | NM_005252 | 28 |
| ZNF407 | zinc finger protein 407 | NM_017757 | 31 |
| ZCCHC2 | zinc finger, CCHC domain containing 2 | NM_017742 | 38 |
| ARNTL2 | aryl hydrocarbon receptor nuclear translocator-like 2 | NM_020183 | 48 |
|  | unnamed protein product; diaminopimelate decarboxylase (AA 1-327); *Bacillus subtilis* lys gene for diaminopimelate decarboxylase (EC 4.1.1.20). | X17013 | 58 |
| SPEC1 | small protein effector 1 of Cdc42 | NM_020239 | 72 |
|  | *Homo sapiens* transcribed sequences | BQ277484 | 101 |
| CBX5 | chromobox homolog 5 (HP1 alpha homolog, *Drosophila*) | NM_012117 | 131 |
| C4.4A | GPI-anchored metastasis-associated protein homolog | NM_014400 | 146 |
| FLJ10525 | hypothetical protein FLJ10525 | NM_018126 | 154 |

TABLE 7

Individual samples
Stable Asthma two-fold decrease

| Common | Description | Genbank | Seq. ID Number |
|---|---|---|---|
| BCL6 | B-cell CLL/lymphoma 6 (zinc finger protein 51) | NM_138931 | 21 |
| TREM1 | triggering receptor expressed on myeloid cells 1 | NM_018643 | 29 |
| RPEL1 | RPEL repeat containing 1 | AB051520 | 51 |
| DNCI1 | dynein, cytoplasmic, intermediate polypeptide 1 | NM_004411 | 85 |
| EPOR | erythropoietin receptor | NM_000121 | 87 |
| LILRB2 | leukocyte immunoglobulin-like receptor, subfamily B (with TM and ITIM domains), member 2 | NM_005874 | 145 |
| HLA-DPB1 | major histocompatibility complex, class II, DP beta 1 | NM_002121 | 147 |
| KCNC3 | potassium voltage-gated channel, Shaw-related subfamily, member 3 | NM_004977 | 166 |

TABLE 8

Individual samples
Stable Asthma three-fold decrease

| Common | Description | Genbank | Seq. ID Number |
|---|---|---|---|
|  | Homo sapiens mRNA; cDNA DKFZp566D053 (from clone DKFZp566D053) | AW611486 | 71 |
| LOC253559 | nectin-like protein 3 | NM_153184 | 95 |
| ZNF483 | zinc finger protein 483 | NM_007169 | 150 |
| ZNF483 | zinc finger protein 483 | NM_133464 | 151 |

TABLE 9

Individual samples
Exacerbated Asthma increases, Stable Asthma no change

| Common | Description | Genbank | Seq. ID Number |
|---|---|---|---|
| KRT24 | keratin 24 | NM_019016 | 14 |
| KRT6A | keratin 6A | NM_005554 | 17 |
| GPR65 | G protein-coupled receptor 65 | NM_003608 | 20 |
| EMR2 | egf-like module containing, mucin-like, hormone receptor-like 2 | NM_013447 | 22 |
| THBD | thrombomodulin | NM_000361 | 23 |
| FPRL1 | formyl peptide receptor-like 1 | NM_001462 | 24 |
| PROK2 | prokineticin 2 | NM_021935 | 26 |
| PDE4B | phosphodiesterase 4B, cAMP-specific (phosphodiesterase E4 dunce homolog, Drosophila) | NM_002600 | 27 |
| HAL | histidine ammonia-lyase | NM_002108 | 30 |
| SLC2A14 | solute carrier family 2 (facilitated glucose transporter), member 14 | NM_153449 | 32 |
| AQP9 | aquaporin 9 | NM_020980 | 33 |
| BCL2A1 | BCL2-related protein A1 | NM_004049 | 34 |
| SERPINB4 | serine (or cysteine) proteinase inhibitor, clade B (ovalbumin), member 4 | NM_002974 | 36 |
| ALDH1A3 | aldehyde dehydrogenase 1 family, member A3 | NM_000693 | 39 |
| CLECSF6 | C-type (calcium dependent, carbohydrate-recognition domain) lectin, superfamily member 6 | NM_016184 | 40 |
| IL1B | interleukin 1, beta | NM_000576 | 41 |
| LILRB1 | leukocyte immunoglobulin-like receptor, subfamily B (with TM and ITIM domains), member 1 | NM_006669 | 42 |
| SLC2A3 | solute carrier family 2 (facilitated glucose transporter), member 3 | NM_006931 | 43 |
| S100A9 | S100 calcium binding protein A9 (calgranulin B) | NM_002965 | 44 |
| PLEK | pleckstrin | NM_002664 | 45 |
| DTNA | dystrobrevin, alpha | NM_001390 | 47 |
| RAI3 | retinoic acid induced 3 | NM_003979 | 49 |
| G0S2 | putative lymphocyte G0/G1 switch gene | NM_015714 | 50 |
| CSF2RB | colony stimulating factor 2 receptor, beta, low-affinity (granulocyte-macrophage) | NM_000395 | 52 |
| PLAUR | plasminogen activator, urokinase receptor | NM_002659 | 53 |
| HIST1H2BH | histone 1, H2bh | NM_003524 | 54 |
| EMP1 | epithelial membrane protein 1 | NM_001423 | 55 |
| TF | transferrin | NM_001063 | 56 |
| PRG1 | proteoglycan, secretory granule | NM_002727 | 57 |

TABLE 9-continued

Individual samples
Exacerbated Asthma increases, Stable Asthma no change

| Common | Description | Genbank | Seq. ID Number |
|---|---|---|---|
| PLEK | pleckstrin | NM_002664 | 59 |
| GPR43 | G protein-coupled receptor 43 | NM_005306 | 60 |
| HIST1H2BC | histone 1, H2bc | NM_003526 | 61 |
| SPRR1A | small proline-rich protein 1A | NM_005987 | 62 |
| ITGAM | integrin, alpha M (complement component receptor 3, alpha; also known as CD11b (p170), macrophage antigen alpha polypeptide) | NM_000632 | 65 |
| SOD2 | superoxide dismutase 2, mitochondrial | NM_000636 | 67 |
| OLR1 | oxidised low density lipoprotein (lectin-like) receptor 1 | NM_002543 | 69 |
| GPR97 | G protein-coupled receptor 97 | NM_170776 | 70 |
| MMP25 | matrix metalloproteinase 25 | NM_022468 | 73 |
| AKR1B10 | synonyms: HIS, HSI, ARL1, ARL-1, ALDRLn, AKR1B11, AKR1B12, MGC14103; aldose reductase-like 1; aldo-keto reductase family 1, member B11 (aldose reductase-like); aldose reductase-like peptide; aldose reductase-related protein; small intestine reductase; go_ | NM_004812 NM_020299* | 74 |
| AKR1B10 | synonyms: HIS, HSI, ARL1, ARL-1, ALDRLn, AKR1B11, AKR1B12, MGC14103; aldose reductase-like 1; aldo-keto reductase family 1, member B11 (aldose reductase-like); aldose reductase-like peptide; aldose reductase-related protein; small intestine reductase; go_ | NM_020299 | 75 |
| HM74 | putative chemokine receptor | NM_006018 | 78 |
| NR4A1 | nuclear receptor subfamily 4, group A, member 1 | NM_002135 | 79 |
| HIST1H1C | histone 1, H1c | NM_005319 | 83 |
|  | *Homo sapiens* transcribed sequences | BQ010718 | 84 |
| SERPINB13 | serine (or cysteine) proteinase inhibitor, clade B (ovalbumin), member 13 | NM_012397 | 86 |
| HIST1H2BK | histone 1, H2bk | NM_080593 | 88 |
| IL1R2 | interleukin 1 receptor, type II | NM_004633 | 90 |
| DUSP5 | dual specificity phosphatase 5 | NM_004419 | 92 |
| TLR4 | toll-like receptor 4 | NM_003266 | 93 |
| CCR1 | chemokine (C—C motif) receptor 1 | NM_001295 | 94 |
| RAI3 | retinoic acid induced 3 | NM_003979 | 96 |
| KRT13 | keratin 13 | NM_153490 | 97 |
| PLAU | plasminogen activator, urokinase | NM_002658 | 98 |
| SLC11A1 | solute carrier family 11 (proton-coupled divalent metal ion transporters), member 1 | NM_000578 | 105 |
| C1QR1 | complement component 1, q subcomponent, receptor 1 | NM_012072 | 106 |
| IL1A | interleukin 1, alpha | NM_000575 | 107 |
| SPRR2B | small proline-rich protein 2B | NM_001017418 | 109 |
| SPRR3 | small proline-rich protein 3 | NM_005416 | 110 |
| MAD | MAX dimerization protein 1 | NM_002357 | 112 |
| CLECSF12 | C-type (calcium dependent, carbohydrate-recognition domain) lectin, super-family member 12 | NM_197953 | 114 |
| SPRR1B | small proline-rich protein 1B (cornifin) | NM_003125 | 117 |
| EAT2 | SH2 domain-containing molecule EAT2 | NM_053282 | 120 |
| PRV1 | polycythemia rubra vera 1 | NM_020406 | 129 |
| S100A2 | S100 calcium binding protein A2 | NM_005978 | 134 |
| CD44 | CD44 antigen (homing function and Indian blood group system) | NM_000610 | 135 |
| JUNB | jun B proto-oncogene | NM_002229 | 139 |
| LILRB2 | leukocyte immunoglobulin-like receptor, subfamily B (with TM and ITIM domains), member 2 | NM_005874 | 145 |
| CPA4 | carboxypeptidase A4 | NM_016352 | 153 |
| LILRB1 | leukocyte immunoglobulin-like receptor, subfamily B (with TM and ITIM domains), member 1 | NM_006669 | 160 |
| FCGR2A | Fc fragment of IgG, low affinity IIa, receptor for (CD32) | NM_021642 | 163 |

*corrected accession number in Genbank

TABLE 10

Individual samples
Exacerbated Asthma decreases, Stable Asthma no change

| Common | Description | Genbank | Seq. ID Number |
|---|---|---|---|
| SF1 | splicing factor 1 | NM_004630 | 11 |
| KCTD7 | potassium channel tetramerisation domain containing 7 | NM_153033 | 12 |
| CLGN | calmegin | NM_004362 | 13 |
| ADCY2 | adenylate cyclase 2 (brain) | NM_020546 | 46 |
| DNAH7 | dynein, axonemal, heavy polypeptide 7 | NM_018897 | 63 |
|  | *Homo sapiens* transcribed sequence with weak similarity to |  |  |

TABLE 10-continued

Individual samples
Exacerbated Asthma decreases, Stable Asthma no change

| Common | Description | Genbank | Seq. ID Number |
|---|---|---|---|
| | protein sp: P39194 (*H. sapiens*) ALU7_HUMAN Alu subfamily SQ sequence contamination warning entry | BX361062 | 66 |
| FLJ23505 | *Homo sapiens* cDNA: FLJ23505 fis, clone LNG03017 | NM_024716 | 68 |
| KIF3A | kinesin family member 3A | NM_007054 | 80 |
| IGFBP7 | insulin-like growth factor binding protein 7 | NM_001553 | 81 |
| TSAP6 | tumor suppressor pHyde; *Homo sapiens* dudulin 2 (TSAP6), mRNA. | NM_182915 | 82 |
| IPW | *Homo sapiens* mRNA; cDNA DKFZp686M12165 (from clone DKFZp686M12165) | BX648788 | 89 |
| PLTP | phospholipid transfer protein | NM_006227 | 91 |
| | gb: BC029442.1/DB_XREF = gi: 20809535/TID = Hs2Affx.1.373/CNT = 1/FEA = FLmRNA/TIER = FL/STK = 1/ NOTE = sequence(s) not in UniGene/DEF = *Homo sapiens*, Similar to immunity associated protein 1, clone MGC: 32707 IMAGE: 4618467, mRNA, complete cds./PROD = Similar to immu | BC029442 | 99 |
| SIAH1 | seven in absentia homolog 1 (*Drosophila*) | NM_003031 | 100 |
| | *Homo sapiens* transcribed sequences | BX107340 | 103 |
| MGC26733 | hypothetical protein MGC26733 | NM_144992 | 104 |
| FLJ40427 | hypothetical protein FLJ40427 | NM_178504 | 108 |
| MYLK | myosin, light polypeptide kinase | NM_053025 | 111 |
| DNAH5 | dynein, axonemal, heavy polypeptide 5 | NM_001369 | 115 |
| DNAH9 | dynein, axonemal, heavy polypeptide 9 | NM_001372 | 116 |
| | *Homo sapiens* cDNA FLJ12411 fis, clone MAMMA1002964. | AK022473 | 118 |
| SLC26A7 | solute carrier family 26, member 7 | NM_052832 | 119 |
| LOC123872 | similar to RIKEN cDNA 4930457P18 | NM_178452 | 121 |
| CHST5 | carbohydrate (N-acetylglucosamine 6-O) sulfotransferase 5 | NM_024533 | 122 |
| | *Homo sapiens* cDNA: FLJ22631 fis, clone HSI06451. | AK026284 | 124 |
| KIAA1688 | KIAA1688 protein | AB051475 | 125 |
| DCDC2 | doublecortin domain containing 2 | NM_016356 | 127 |
| | *Homo sapiens* transcribed sequences | CD698727 | 128 |
| SPAG8 | sperm associated antigen 8 | NM_012436 | 130 |
| LOC138428 | hypothetical protein LOC286207 | AL833241 | 133 |
| | *Homo sapiens* cDNA: FLJ22781 fis, clone KAIA1958. | AK026434 | 136 |
| | *Homo sapiens* cDNA FLJ12093 fis, clone HEMBB1002603. | AK022155 | 137 |
| ATM | ataxia telangiectasia mutated (includes complementation groups A, C and D) | NM_000051 | 138 |
| FLJ13621 | hypothetical protein FLJ13621 | NM_025009 | 140 |
| HPX | hemopexin | NM_000613 | 141 |
| | *Homo sapiens* cDNA: FLJ23502 fis, clone LNG02862 | AK027155 | 142 |
| DNAI2 | dynein, axonemal, intermediate polypeptide 2 | NM_023036 | 143 |
| LOC165186 | UI-H-EZ1-bbk-j-02-0-UI.s1 NCI_CGAP_Ch2 *Homo sapiens* cDNA clone UI-H-EZ1-bbk-j-02-0-UI 3', mRNA sequence.; ESTs, Weakly similar to T00057 hypothetical protein KIAA0423 - human (fragment) [*H. sapiens*] | NM_199280 | 144 |
| | *Homo sapiens* mRNA; cDNA DKFZp761D2417 (from clone DKFZp761D2417) | AL831856 | 148 |
| | UI-E-EJO-ahi-c-20-0-UI.r1 UI-E-EJO *Homo sapiens* cDNA clone UI-E-EJO-ahi-c-20-0-UI 5', mRNA sequence. | BM712946 | 149 |
| FLJ14665 | Start codon is not identified.; *Homo sapiens* mRNA for KIAA1864 protein, partial cds. | AB058767 | 155 |
| MGC16202 | hypothetical protein MGC16202 | NM_032373 | 156 |
| | *Homo sapiens* LOH11CR1P gene, loss of heterozygosity, 11, chromosomal region 1 gene P product | CA478747 | 157 |
| LOC146177 | *Homo sapiens* hypothetical protein LOC146177 (LOC146177), mRNA. | NM_175059 | 158 |
| SCARF2 | scavenger receptor class F, member 2 | NM_153334 | 159 |
| MGC40053 | hypothetical protein MGC40053 | NM_152583 | 161 |
| LOC339005 | *Homo sapiens* cDNA FLJ33935 fis, clone CTONG2017910. | AK091254 | 162 |
| C18orf1 | alternatively spliced; beta-1 form; possible membrane-spanning protein; clone 22; *Homo sapiens* chromosome 18 open reading frame 1 (C18orf1), mRNA. | NM_181481 | 164 |
| MYEF2 | myelin expression factor 2 | NM_016132 | 165 |
| DNAH3 | dynein, axonemal, heavy polypeptide 3 | NM_017539 | 167 |

TABLE 11

Individual samples
Stable Asthma increases, Exacerbated Asthma no change

| Common | Description | Genbank | Seq. ID Number |
|---|---|---|---|
|  | *Homo sapiens* transcribed sequences | AI476722 | 37 |
| ZCCHC2 | zinc finger, CCHC domain containing 2 | NM_017742 | 38 |
| CBX5 | chromobox homolog 5 (HP1 alpha homolog, *Drosophila*) | NM_012117 | 131 |
| FLJ10525 | hypothetical protein FLJ10525 | NM_018126 | 154 |

TABLE 12

Individual samples
Stable Asthma decreases, Exacerbated Asthma no change

| Common | Description | Genbank | Seq. ID Number |
|---|---|---|---|
| BCL6 | B-cell CLL/lymphoma 6 (zinc finger protein 51) | NM_138931 | 21 |
|  | *Homo sapiens* mRNA; cDNA DKFZp566D053 (from clone DKFZp566D053) | AW611486 | 71 |
| DNCI1 | dynein, cytoplasmic, intermediate polypeptide 1 | NM_004411 | 85 |
| EPOR | erythropoietin receptor | NM_000121 | 87 |
| LOC253559 | nectin-like protein 3 | NM_153184 | 95 |
| HLA-DPB1 | major histocompatibility complex, class II, DP beta 1 | NM_002121 | 147 |
| ZNF483 | zinc finger protein 483 | NM_007169 | 150 |
| ZNF483 | zinc finger protein 483 | NM_133464 | 151 |
| KCNC3 | potassium voltage-gated channel, Shaw-related subfamily, member 3 | NM_004977 | 166 |

TABLE 13

Individual samples
Stable Asthma increases, Exacerbated Asthma increases

| Common | Description | Genbank | Seq. ID Number |
|---|---|---|---|
| SOSTDC1 | sclerostin domain containing 1 | NM_015464 | 15 |
| BM039 | uncharacterized bone marrow protein BM039 | NM_018455 | 16 |
| CALB1 | calbindin 1, 28 kDa | NM_004929 | 18 |
| FOS | v-fos FBJ murine osteosarcoma viral oncogene homolog | NM_005252 | 28 |
| ZNF407 | zinc finger protein 407 | NM_017757 | 31 |
| CYP1A1 | cytochrome P450, family 1, subfamily A, polypeptide 1 | NM_000499 | 35 |
| ARNTL2 | aryl hydrocarbon receptor nuclear translocator-like 2 | NM_020183 | 48 |
|  | unnamed protein product; diaminopimelate decarboxylase (AA 1-327); *Bacillus subtilis* lys gene for diaminopimelate decarboxylase (EC 4.1.1.20). | X17013 | 58 |
| SPEC1 | small protein effector 1 of Cdc42 | NM_020239 | 72 |
| EMP1 | epithelial membrane protein 1 | NM_001423 | 76 |
| SCEL | sciellin | NM_144777 | 77 |
|  | *Homo sapiens* transcribed sequences | BQ277484 | 101 |
| DCP2 | decapping enzyme hDcp2 | NM_152624 | 126 |
| RAB35 | RAB35, member RAS oncogene family | NM_006861 | 132 |
| C4.4A | GPI-anchored metastasis-associated protein homolog | NM_014400 | 146 |
| SLC30A7 | solute carrier family 30 (zinc transporter), member 7 | NM_133496 | 152 |

TABLE 14

Individual samples
Inverse Changes
Stable Asthma increases, Exacerbated Asthma Decrease or Stable Asthma decreases,
Exacerbated Asthma increases

| Common | Description | Genbank | Seq. ID Number |
|---|---|---|---|
| TREM1 | triggering receptor expressed on myeloid cells 1 | NM_018643 | 29 |
| RPEL1 | RPEL repeat containing 1 | AB051520 | 51 |
|  | UI-H-BW0-aim-d-12-0-UI.s1 NCI_CGAP_Sub6 *Homo sapiens* cDNA clone IMAGE: 2729902 3', mRNA sequence. | AW294722 | 123 |

TABLE 14-continued

Individual samples
Inverse Changes
Stable Asthma increases, Exacerbated Asthma Decrease or Stable Asthma decreases,
Exacerbated Asthma increases

| Common | Description | Genbank | Seq. ID Number |
|---|---|---|---|
| LILRB2 | leukocyte immunoglobulin-like receptor, subfamily B (with TM and ITIM domains), member 2 | NM_005874 | 145 |

TABLE 15

Pooled samples
Exacerbated Asthma two-fold increase

| Common | Description | Genbank | Seq. ID Number |
|---|---|---|---|
| GPR65 | G protein-coupled receptor 65 | NM_003608 | 20 |
| HAL | histidine ammonia-lyase | NM_002108 | 30 |
| SLC2A14 | solute carrier family 2 (facilitated glucose transporter), member 14 | NM_153449 | 32 |
| PLAUR | plasminogen activator, urokinase receptor | NM_002659 | 53 |
| TF | transferrin | NM_001063 | 56 |
| PLEK | pleckstrin | NM_002664 | 59 |
| HIST1H2BC | histone 1, H2bc | NM_003526 | 61 |
| GPR97 | G protein-coupled receptor 97 | NM_170776 | 70 |
| HIST1H2BK | histone 1, H2bk | NM_080593 | 88 |
| IL1R2 | interleukin 1 receptor, type II | NM_004633 | 90 |
| DUSP5 | dual specificity phosphatase 5 | NM_004419 | 92 |
| TLR4 | toll-like receptor 4 | NM_003266 | 93 |

TABLE 16

Pooled samples
Exacerbated Asthma three-fold increase

| Common | Description | Genbank | Seq. ID Number |
|---|---|---|---|
| KRT24 | keratin 24 | NM_019016 | 14 |
| SOSTDC1 | sclerostin domain containing 1 | NM_015464 | 15 |
| KRT6A | keratin 6A | NM_005554 | 17 |
| CALB1 | calbindin 1, 28 kDa | NM_004929 | 18 |
| FCGR2B | Fc fragment of IgG, low affinity IIb, receptor for (CD32) | NM_004001 | 19 |
| EMR2 | egf-like module containing, mucin-like, hormone receptor-like 2 | NM_013447 | 22 |
| FPRL1 | formyl peptide receptor-like 1 | NM_001462 | 24 |
| PDE4B | phosphodiesterase 4B, cAMP-specific (phosphodiesterase E4 dunce homolog, *Drosophila*) | NM_002600 | 27 |
| FOS | v-fos FBJ murine osteosarcoma viral oncogene homolog | NM_005252 | 28 |
| TREM1 | triggering receptor expressed on myeloid cells 1 | NM_018643 | 29 |
| ZNF407 | zinc finger protein 407 | NM_017757 | 31 |
| AQP9 | aquaporin 9 | NM_020980 | 33 |
| BCL2A1 | BCL2-related protein A1 | NM_004049 | 34 |
| CYP1A1 | cytochrome P450, family 1, subfamily A, polypeptide 1 | NM_000499 | 35 |
| ALDH1A3 | aldehyde dehydrogenase 1 family, member A3 | NM_000693 | 39 |
| CLECSF6 | C-type (calcium dependent, carbohydrate-recognition domain) lectin, superfamily member 6 | NM_016184 | 40 |
| IL1B | interleukin 1, beta | NM_000576 | 41 |
| LILRB1 | leukocyte immunoglobulin-like receptor, subfamily B (with TM and ITIM domains), member 1 | NM_006669 | 42 |
| SLC2A3 | solute carrier family 2 (facilitated glucose transporter), member 3 | NM_006931 | 43 |
| S100A9 | S100 calcium binding protein A9 (calgranulin B) | NM_002965 | 44 |
| PLEK | pleckstrin | NM_002664 | 45 |
| DTNA | dystrobrevin, alpha | NM_001390 | 47 |
| RAI3 | retinoic acid induced 3 | NM_003979 | 49 |
| G0S2 | putative lymphocyte G0/G1 switch gene | NM_015714 | 50 |
| RPEL1 | RPEL repeat containing 1 | AB051520 | 51 |
| CSF2RB | colony stimulating factor 2 receptor, beta, low-affinity (granulocyte-macrophage) | NM_000395 | 52 |
| EMP1 | epithelial membrane protein 1 | NM_001423 | 55 |

TABLE 16-continued

Pooled samples
Exacerbated Asthma three-fold increase

| Common | Description | Genbank | Seq. ID Number |
|---|---|---|---|
| PRG1 | proteoglycan 1, secretory granule | NM_002727 | 57 |
| | unnamed protein product; diaminopimelate decarboxylase (AA 1-327); *Bacillus subtilis* lys gene for diaminopimelate decarboxylase (EC 4.1.1.20). | X17013 | 58 |
| GPR43 | G protein-coupled receptor 43 | NM_005306 | 60 |
| SPRR1A | small proline-rich protein 1A | NM_005987 | 62 |
| SOD2 | superoxide dismutase 2, mitochondrial | NM_000636 | 67 |
| OLR1 | oxidised low density lipoprotein (lectin-like) receptor 1 | NM_002543 | 66 |
| AKR1B10 | synonyms: HIS, HSI, ARL1, ARL-1, ALDRLn, AKR1B11, AKR1B12, MGC14103; aldose reductase-like 1; aldo-keto reductase family 1, member B11 (aldose reductase-like); aldose reductase-like peptide; aldose reductase-related protein; small intestine reductase; go_ | NM_004812 | 74 |
| AKR1B10 | synonyms: HIS, HSI, ARL1, ARL-1, ALDRLn, AKR1B11, AKR1B12, MGC14103; aldose reductase-like 1; aldo-keto reductase family 1, member B11 (aldose reductase-like); aldose reductase-like peptide; aldose reductase-related protein; small intestine reductase; go_ | NM_020299 | 75 |
| EMP1 | epithelial membrane protein 1 | NM_001423 | 76 |
| HM74 | putative chemokine receptor | NM_006018 | 78 |
| HIST1H1C | histone 1, H1c | NM_005319 | 83 |
| CCR1 | chemokine (C—C motif) receptor 1 | NM_001295 | 94 |
| KRT13 | keratin 13 | NM_153490 | 97 |
| PLAU | plasminogen activator, urokinase | NM_002658 | 98 |
| IL1A | interleukin 1, alpha | NM_000575 | 107 |
| SPRR2B | small proline-rich protein 2B | NM_001017418 | 109 |
| SPRR1B | small proline-rich protein 1B (cornifin) | NM_003125 | 117 |
| S100A2 | S100 calcium binding protein A2 | NM_005978 | 134 |
| LILRB2 | leukocyte immunoglobulin-like receptor, subfamily B (with TM and ITIM domains), member 2 | NM_005874 | 145 |
| C4.4A | GPI-anchored metastasis-associated protein homolog | NM_014400 | 146 |
| CPA4 | carboxypeptidase A4 | NM_016352 | 153 |
| LILRB1 | leukocyte immunoglobulin-like receptor, subfamily B (with TM and ITIM domains), member 1 | NM_006669 | 160 |
| FCGR2A | Fc fragment of IqG, low affinity IIa, receptor for (CD32) | NM_021642 | 163 |

* corrected accession number in Genbank

TABLE 17

Pooled samples
Exacerbated Asthma two-fold decrease

| Common | Description | Genbank | Seq. ID Number |
|---|---|---|---|
| CLGN | calmegin | NM_004362 | 13 |
| FLJ13615 | hypothetical protein FLJ13615 | NM_025114 | 25 |
| FLJ23505 | *Homo sapiens* cDNA: FLJ23505 fis, clone LNG03017 | NM_024716 | 68 |
| KIF3A | kinesin family member 3A | NM_007054 | 80 |
| IGFBP7 | insulin-like growth factor binding protein 7 | NM_001553 | 81 |
| TSAP6 | tumor suppressor pHyde; *Homo sapiens* dudulin 2 (TSAP6), mRNA. | NM_182915 | 82 |
| PLTP | phospholipid transfer protein | NM_006227 | 91 |
| SIAH1 | seven in absentia homolog 1 (*Drosophila*) | NM_003031 | 100 |
| TCF2 | transcription factor 2, hepatic; LF-B3; variant hepatic nuclear factor | NM_006481 | 113 |
| LOC123872 | similar to RIKEN cDNA 4930457P18 | NM_178452 | 121 |
| DCDC2 | doublecortin domain containing 2 | NM_016356 | 127 |
| HPX | hemopexin | NM_000613 | 141 |
| DNAI2 | dynein, axonemal, intermediate polypeptide 2 | NM_023036 | 143 |
| C18orf1 | alternatively spliced; beta-1 form; possible membrane-spanning protein; clone 22; *Homo sapiens* chromosome 18 open reading frame 1 (C18orf1), mRNA. | NM_181481 | 164 |

TABLE 18

Pooled samples
Exacerbated Asthma three-fold decrease

| Common | Description | Genbank | Seq. ID Number |
|---|---|---|---|
| SF1 | splicing factor 1 | NM_004630 | 11 |
| KCTD7 | potassium channel tetramerisation domain containing 7 | NM_153033 | 12 |
| MYLK | myosin, light polypeptide kinase | NM_053025 | 111 |
|  | *Homo sapiens* cDNA FLJ12411 fis, clone MAMMA1002964. | AK022473 | 118 |

TABLE 19

Pooled samples
Stable Asthma two-fold increase

| Common | Description | Genbank | Seq. ID Number |
|---|---|---|---|
| FOS | v-fos FBJ murine osteosarcoma viral oncogene homolog | NM_005252 | 28 |
| AQP9 | aquaporin 9 | NM_020980 | 33 |
| IL1B | interleukin 1, beta | NM_000576 | 41 |
| S100A9 | S100 calcium binding protein A9 (calgranulin B) | NM_002965 | 44 |
| PLEK | pleckstrin | NM_002664 | 45 |
| OLR1 | oxidised low density lipoprotein (lectin-like) receptor 1 | NM_002543 | 69 |
| JUNB | jun B proto-oncogene | NM_002229 | 139 |

TABLE 20

Pooled samples
Stable Asthma three-fold increase

| Common | Description | Genbank | Seq. ID Number |
|---|---|---|---|
| KRT6A | keratin 6A | NM_005554 | 17 |
| CALB1 | calbindin 1, 28 kDa | NM_004929 | 18 |
| PDE4B | phosphodiesterase 4B, cAMP-specific (phosphodiesterase E4 dunce homolog, *Drosophila*) | NM_002600 | 27 |
| HAL | histidine ammonia-lyase | NM_002108 | 30 |
| ZNF407 | zinc finger protein 407 | NM_017757 | 31 |
| CYP1A1 | cytochrome P450, family 1, subfamily A, polypeptide 1 | NM_000499 | 35 |
| LILRB1 | leukocyte immunoglobulin-like receptor, subfamily B (with TM and ITIM domains), member 1 | NM_006669 | 42 |
| DTNA | dystrobrevin, alpha | NM_001390 | 47 |
|  | unnamed protein product; diaminopimelate decarboxylase (AA 1-327); *Bacillus subtilis* lys gene for diaminopimelate decarboxylase (EC 4.1.1.20). | X17013 | 58 |
| IL1A | interleukin 1, alpha | NM_000575 | 107 |
| LILRB2 | leukocyte immunoglobulin-like receptor, subfamily B (with TM and ITIM domains), member 2 | NM_005874 | 145 |

TABLE 21

Pooled samples
Stable Asthma two-fold decrease

| Common | Description | Genbank | Seq. ID Number |
|---|---|---|---|
| SF1 | splicing factor 1 | NM_004630 | 11 |
| FCGR2B | Fc fragment of IgG, low affinity IIb, receptor for (CD32) | NM_004001 | 19 |
| BCL6 | B-cell CLL/lymphoma 6 (zinc finger protein 51) | NM_138931 | 21 |
| IPW | *Homo sapiens* mRNA; cDNA DKFZp686M12165 (from clone DKFZp686M12165) | BX648788 | 89 |
| TCF2 | transcription factor 2, hepatic; LF-B3; variant hepatic nuclear factor | NM_006481 | 113 |
| SPAG8 | sperm associated antigen 8 | NM_012436 | 130 |

TABLE 22

Pooled samples
Stable Asthma three-fold decrease

| Common | Description | Genbank | Seq. ID Number |
|---|---|---|---|
| SOSTDC1 | sclerostin domain containing 1 | NM_015464 | 15 |
| RPEL1 | RPEL repeat containing 1 | AB051520 | 51 |

TABLE 22-continued

Pooled samples
Stable Asthma three-fold decrease

| Common | Description | Genbank | Seq. ID Number |
|---|---|---|---|
| PLAU | plasminogen activator, urokinase | NM_002658 | 98 |
| C12orf6 | chromosome 12 open reading frame 6 | NM_020367 | 102 |

TABLE 23

Genes $F_{ST} > 0.25$ between Caucasians and Han Chinese from 161 gene dataset

| Common | Description | Genbank | Seq. ID Number |
|---|---|---|---|
| PDE4B | phosphodiesterase 4B, cAMP-specific (phosphodiesterase E4 dunce homolog, *Drosophila*) | NM_002600 | 27 |
| ADCY2 | adenylate cyclase 2 (brain) | NM_020546 | 46 |
| KIF3A | kinesin family member 3A | NM_007054 | 80 |
| HIST1H1C | histone 1, H1c | NM_005319 | 83 |
| PLAU | plasminogen activator, urokinase | NM_002658 | 98 |
| FLJ40427 | hypothetical protein FLJ40427 | NM_178504 | 108 |
| SPRR2B | small proline-rich protein 2B | NM_001017418 | 109 |
| MYLK | myosin, light polypeptide kinase | NM_053025 | 111 |
| DNAH5 | dynein, axonemal, heavy polypeptide 5 | NM_001369 | 115 |
| SLC26A7 | solute carrier family 26, member 7 | NM_052832 | 119 |
| CHST5 | carbohydrate (N-acetylglucosamine 6-O) sulfotransferase 5 | NM_024533 | 122 |
| ZNF483 | zinc finger protein 483 | NM_007169 | 150 |
| ZNF483 | zinc finger protein 483 | NM_133464 | 151 |
| SCARF2 | scavenger receptor class F, member 2 | NM_153334 | 159 |
| C18orf1 | alternatively spliced; beta-1 form; possible membrane-spanning protein; clone 22; *Homo sapiens* chromosome 18 open reading frame 1 (C18Sorf1), mRNA. | NM_181481 | 164 |
| MYEF2 | myelin expression factor 2 | NM_016132 | 165 |
| KCNC3 | potassium voltage-gated channel, Shaw-related subfamily, member 3 | NM_004977 | 166 |

* corrected accession number in Genbank

TABLE 24

Genes $0.15 < F_{ST} < 0.25$ between Caucasians and Han Chinese from 161 gene dataset

| Common | Description | Genbank | Seq. ID Number |
|---|---|---|---|
| CALB1 | calbindin 1, 28 kDa | NM_004929 | 18 |
| HAL | histidine ammonia-lyase | NM_002108 | 30 |
| ZNF407 | zinc finger protein 407 | NM_017757 | 31 |
| SLC2A14 | solute carrier family 2 (facilitated glucose transporter), member 14 | NM_153449 | 32 |
| BCL2A1 | BCL2-related protein A1 | NM_004049 | 34 |
| ZCCHC2 | zinc finger, CCHC domain containing 2 | NM_017742 | 38 |
| ALDH1A3 | aldehyde dehydrogenase 1 family, member A3 | NM_000693 | 39 |
| PLEK | pleckstrin | NM_002664 | 45 |
| DTNA | dystrobrevin, alpha | NM_001390 | 47 |
| ARNTL2 | aryl hydrocarbon receptor nuclear translocator-like 2 | NM_020183 | 48 |
| EMP1 | epithelial membrane protein 1 | NM_001423 | 55 |
| PRG1 | proteoglycan 1, secretory granule | NM_002727 | 57 |
| DNAH7 | dynein, axonemal, heavy polypeptide 7 | NM_018897 | 63 |
| SCEL | sciellin | NM_144777 | 77 |
| DNCI1 | dynein, cytoplasmic, intermediate polypeptide 1 | NM_004411 | 85 |
| MGC26733 | hypothetical protein MGC26733 | NM_144992 | 104 |
| TCF2 | transcription factor 2, hepatic; LF-B3; variant hepatic nuclear factor | NM_006481 | 113 |
| CLECSF12 | C-type (calcium dependent, carbohydrate-recognition domain) lectin, superfamily member 12 | NM_197953 | 114 |
| DNAH9 | dynein, axonemal, heavy polypeptide 9 | NM_001372 | 116 |
| EAT2 | SH2 domain-containing molecule EAT2 | NM_053282 | 120 |
| PRV1 | polycythemia rubra vera 1 | NM_020406 | 129 |
| DNAI2 | dynein, axonemal, intermediate polypeptide 2 | NM_023036 | 143 |
| LOC165186 | UI-H-EZ1-bbk-j-02-0-UI.s1 NCI_CGAP_Ch2 *Homo sapiens* cDNA clone UI-H-EZ1-bbk-j-02-0-UI 3', mRNA sequence.; ESTs, Weakly similar to T00057 hypothetical protein KIAA0423 - human (fragment) [*H. sapiens*] | NM_199280 | 144 |

TABLE 24-continued

Genes 0.15 < $F_{ST}$ < 0.25 between Caucasians and Han Chinese from 161 gene dataset

| Common | Description | Genbank | Seq. ID Number |
|---|---|---|---|
| SLC30A7 | solute carrier family 30 (zinc transporter), member 7 | NM_133496 | 152 |
| LILRB1 | leukocyte immunoglobulin-like receptor, subfamily B (with TM and ITIM domains), member 1 | NM_006669 | 160 |
| DNAH3 | dynein, axonemal, heavy polypeptide 3 | NM_017539 | 167 |

Other variations or embodiments of the invention will also be apparent to one of ordinary skill in the art from the above figures, tables, and description. Thus, the forgoing embodiments are not to be construed as limiting the scope of this invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07919240B2). An electronic copy of the "Sequence Listing" will also be available from the USPTO upon request and payment of the fee set forth in 37 CFR 1.19(b)(3).

What is claimed is:

1. A method to evaluate a patient, the method comprising subjecting a tissue sample from a human patient with asthma to gene analysis, the analysis resulting in an expression profile of at least one gene activated in lungs of a human patient with asthma, comparing the patient's gene expression profile with a gene expression profile for stable asthma and a gene expression profile for exacerbated asthma, and determining whether the patient has a propensity for at least one of stable asthma or exacerbated asthma based on at least a two-fold difference between at least one gene in the patient's gene expression profile and the stable asthma or exacerbated asthma expression profile, wherein the patient has a propensity for stable asthma when the at least two-fold difference is between the patient's gene expression profile and the gene expression profile for exacerbated asthma, or the patient has a propensity for exacerbated asthma when the at least two-fold difference is between the patient's gene expression profile and the gene expression profile for stable asthma.

2. The method of claim 1 based on at least a three-fold difference.

3. The method of claim 1 wherein the tissue is nasal respiratory epithelium.

4. The method of claim 1 comparing a cluster of genes.

5. The method of claim 1 or claim 2 wherein the gene that has the difference between the patient's gene expression profile and the stable asthma gene expression profile is at least one of SEQ ID NOS: 11-14, 17, 20, 22-24, 26-27, 30, 32-34, 36, 39-47, 49-50, 52-57, 59-62, 65-70, 73-75, 78-84, 86, 88-94, 96-100, 103-112, 114-122, 124-125, 127-130, 133-145, 148-149, 153, 155-165, or 167, and the difference indicates a propensity for exacerbated asthma.

6. The method of claim 1 or claim 2 wherein the gene that has the difference between the patient's gene expression profile and the exacerbated asthma gene expression profile is at least one of SEQ ID NOS: 21, 37-38, 71, 85, 87, 95, 131, 147, 150-151, 154, or 166, and the difference indicates a propensity for stable asthma.

7. The method of claim 1 wherein the patient is a child.

8. A diagnostic method comprising subjecting a nasal respiratory epithelium sample of a patient to gene analysis to obtain a tissue expression profile, and diagnosing exacerbated asthma in the patient if at least a two-fold increase between at least one of SEQ ID NOS: 14-18, 20, 22-24, 26-36, 39-45, 47-62, 65, 67, 69-70, 72-79, 83-84, 86, 88, 90, 92-94, 96-98, 101, 105-107, 109-110, 112, 114, 117, 120, 126, 129, 132, 134-135, 139, 145-146, 152-153, 160, or 163 in the patient tissue expression profile over a control tissue expression profile is present.

9. A diagnostic method comprising subjecting a nasal respiratory epithelium sample of a patient to gene analysis to obtain a tissue expression profile, and diagnosing exacerbated asthma in the patient if at least a two-fold decrease in a at least one of SEQ ID NO: 11-13, 46, 63, 66, 68, 80-82, 89, 91, 99-100, 103-104, 108, 111, 115-116, 118-119, 121-125, 127-128, 130, 133, 136-138, 140-144, 148-149, 155-159, 161-162, 164-165, or 167 in the patient tissue expression profile over a control tissue expression profile is present.

10. A diagnostic method comprising subjecting a nasal respiratory epithelium sample of a patient to gene analysis to obtain a tissue expression profile, and diagnosing stable asthma in the patient if at least a two-fold increase between at least one of SEQ ID NOS: 15-16, 18, 28, 31, 35, 37-38, 48, 58, 72, 76-77, 101, 123, 126, 131-132, 146, 152, or 154 in the patient tissue expression profile over a control tissue expression profile is present.

11. A diagnostic method comprising
subjecting a nasal respiratory epithelium sample of a patient to gene analysis to obtain a tissue expression profile, and
diagnosing stable asthma in the patient if at least a two-fold decrease in at least one of SEQ ID NOS: 21, 29, 51, 71, 85, 87, 95, 145, 147, 150-151, or 166 in the patient tissue expression profile over a control tissue expression profile is present.

12. The method of any one of claim 8, 9, 10, or 11 further comprising identifying at least one gene for prophylactic or therapeutic intervention.

* * * * *

UNITED STATES PATENT AND TRADEMARK OFFICE
CERTIFICATE OF CORRECTION

| | | |
|---|---|---|
| PATENT NO. | : 7,919,240 B2 | Page 1 of 1 |
| APPLICATION NO. | : 11/314565 | |
| DATED | : April 5, 2011 | |
| INVENTOR(S) | : Hershey et al. | |

It is certified that error appears in the above-identified patent and that said Letters Patent is hereby corrected as shown below:

Column 36

Line 29, before "least", please insert

-- file and the exacerbated asthma gene expression profile is at --

Signed and Sealed this

Seventeenth Day of May, 2011

David J. Kappos
*Director of the United States Patent and Trademark Office*